US012805758B2

(12) United States Patent
Zhang et al.

(10) Patent No.: US 12,805,758 B2
(45) Date of Patent: Nov. 24, 2026

(54) REAL-TIME SINGLES-BASE CARDIO-RESPIRATORY MOTION TRACKING FOR MOTION-FREE PHOTON IMAGING

(71) Applicant: The Regents of the University of California, Oakland, CA (US)

(72) Inventors: Xuezhu Zhang, Davis, CA (US); Jinyi Qi, Davis, CA (US); Zhaoheng Xie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 212 days.

(21) Appl. No.: 18/712,010

(22) PCT Filed: Jan. 20, 2023

(86) PCT No.: PCT/US2023/061039
§ 371 (c)(1),
(2) Date: May 21, 2024

(87) PCT Pub. No.: WO2023/141603
PCT Pub. Date: Jul. 27, 2023

(65) Prior Publication Data

US 2024/0407672 A1 Dec. 12, 2024

Related U.S. Application Data

(60) Provisional application No. 63/301,404, filed on Jan. 20, 2022.

(51) Int. Cl.
*A61B 5/113* (2006.01)
*A61B 6/03* (2006.01)
*A61B 6/42* (2024.01)

(52) U.S. Cl.
CPC ................ *A61B 5/113* (2013.01); *A61B 6/03* (2013.01); *A61B 6/4241* (2013.01)

(58) Field of Classification Search
CPC ......... A61B 5/113; A61B 6/03; A61B 6/4241; A61B 5/055; A61B 6/5288; A61B 6/503; A61B 6/037
See application file for complete search history.

(56) References Cited

U.S. PATENT DOCUMENTS

2019/0133542 A1* 5/2019 Li ........................ A61B 6/5247
2020/0302619 A1 9/2020 Lu et al.
2021/0196219 A1* 7/2021 Jansen .................. A61B 6/037

* cited by examiner

*Primary Examiner* — Kiho Kim
(74) *Attorney, Agent, or Firm* — Byrne Poh LLP

(57) ABSTRACT

Various techniques are provided for performing real-time subject-motion-tracking during photon imaging by applying various data processing techniques on raw photon-events data generated by photon imaging scanners. In one aspect, a process of performing real-time subject-motion tracking during photon imaging begins by receiving multiple channels of raw singles-event data from a set of detector groups of the photon scanner while scanning a live subject. For each received channel of raw singles-event data, a singles-rate time series is generated based on a predetermined temporal resolution. Next, the set of singles-rate time series corresponding to the set of detector groups is combined to generate an overall singles-rate time series. Subsequently, the overall singles-rate time series is processed to extract in real-time one or more motion signals corresponding to one or more physiological motions of the live subject while the live subject is being scanned.

38 Claims, 10 Drawing Sheets

REAL-TIME SINGLES-BASE CARDIO-RESPIRATORY MOTION TRACKING FOR MOTION-FREE PHOTON IMAGING

CROSS-REFERENCE TO RELATED APPLICATION

This application claims the benefit of U.S. Provisional Patent Application Ser. No. 63/301,404, entitled "Real-Time Motion Tracking for Photon Imaging,", filed on 20 Jan. 2022, the contents of which are incorporated by reference herein.

GOVERNMENT LICENSE RIGHTS

This invention was made with U.S. government support under NIH grant R01-CA206187. The U.S. government has certain rights in the invention.

BACKGROUND

Field

The disclosed embodiments generally relate to the field of quantitative photon imaging. More specifically, the disclosed embodiments relate to techniques for providing real-time subject motion tracking (e.g., cardiac and respiratory motions) on photon imaging (e.g., positron emission tomography or PET, single photon emission computed tomography or SPECT, etc.) for oncologic, cardiovascular and respiratory system function diagnoses without additional external devices (e.g., ECGs or breathing belts).

Related Art

Positron emission tomography (PET) is a molecular imaging system widely used in clinical research and healthcare that has the ability to observe in-vivo molecular-level biomedical and physiological process in living subjects. Although the state-of-the-art PET is able to offer good image quality, cardio-respiratory motion of the subject remains a degradation factor leading to reduced detection accuracy for many cancerous, neurological and cardiovascular diseases, thereby negatively influencing the diagnosis and treatment. To eliminate such motion artifacts, data-driven approaches have been intensively studied for PET motion correction. However, existing data-driven techniques require substantial data processing power and time, and therefore cannot extract cardio-respiratory motion signals in real-time. As a result, these existing data-driven techniques are not suitable for routine uses of a PET during daily scans.

Hence, what is needed is a data-driven technique that enables real-time cardio-respiratory motion tracking during PET imaging without the drawbacks of the existing techniques.

SUMMARY

Various techniques are disclosed for performing real-time subject-motion-tracking during photon (e.g., PET and SPECT) imaging by applying various data processing techniques on raw photon-events data generated by photon imaging (PET and SPECT) scanners. Unlike existing data-driven motion-correction techniques, the disclosed techniques utilize the intrinsic real-time photon (in particular the singles) counting capabilities in these photon imaging systems, and are designed to recover gating signals of the subject motions (e.g., cardiac and respiratory motions) from the raw photon-events data with high temporal resolutions. The disclosed real-time motion-tracking techniques can be integrated with existing photon imaging systems as a built-in software tool or as part of the data acquisition hardware to extract cardio-respiratory motion information directly from the raw scanner data.

More specifically, the disclosed motion-tracking techniques can first construct time-count curves (TCCs) or count-rate time series (CRTSs) directly from raw singles data. The motion-tracking techniques subsequently recover gating signals of the target motions (e.g., the cardiac motion and/or the respiratory motion) from these event-rate time series. In some embodiments, the disclosed motion-tracking techniques are configured to extract a periodic time series signal associated with a tracked motion of large organs (e.g., the heart beating or the lung breathing) from the corresponding TCCs/CRTSs. Specifically, frequency domain analyses and band-pass filtering can be applied to these TCCs/CRTSs based on the characteristic motion periods/frequencies of the large organ. The recovered periodic temporal signal can then serve as the gating signal for reconstructing the motion-free dynamic photon (e.g., PET) scanning images.

The disclosed motion-tracking techniques provide significant advantages over the existing data-driven motion-tracking techniques because of the ability to extract motion (e.g., cardio-respiratory) signals in real-time. Moreover, the disclosed motion-tracking techniques can potentially replace conventional external monitoring techniques for cardiac motions, such as electrocardiogram (EKG or ECG), as well as for respiratory motions, such as breathing belts or optical markers/video trackers. The disclosed real-time motion-tracking techniques can be integrated into existing photon imaging systems as a part of the data-processing software or a part of the data acquisition hardware. Due to the similar operating principles of photon-counting related systems, the disclosed motion-tracking techniques are not only applicable to PET and SPECT imaging systems, but can be integrated with other types of high-energy photon imaging modalities, such as photon-counting computed tomography (PCCT), X-ray CT, planar gamma camera, among others.

The disclosed motion-tracking techniques have demonstrated both high effectiveness and high accuracy in tracking cardio-respiratory motion signals in a wide range of human subjects. Compared with the conventional data-driven techniques based on list-mode events, the disclosed techniques can directly extract the cardio-respiratory gating information from the count rates without any computation in mapping between the projection space and the image space. The disclosed motion-tracking techniques allow the cardio-respiratory motion information from fast and/or dynamic PET scans to be extracted directly from the intrinsic singles counts prior to the coincidence sorting procedure.

In one aspect, a process of performing real-time subject-motion tracking during photon imaging on a photon scanner is disclosed. This process may begin by receiving multiple channels of raw singles-event data from a set of detector groups of the photon scanner while scanning a live subject. For each received channel of raw singles-event data, the process then generates a singles-rate time series based on a predetermined temporal resolution. Next, the process combines the set of singles-rate time series corresponding to the set of detector groups to generate an overall singles-rate time series. The process subsequently processes the weighted-sum singles-rate time series to extract in real-time one or more motion signals corresponding to one or more physiological motions of the live subject while the live subject is being scanned.

In some embodiments, the set of detector groups is associated with one or more detector rings arranged along an axial direction of the photon scanner.

In some embodiments, the photon scanner includes a single detector ring formed by a set of detector blocks, and prior to receiving the multiple channels of raw singles-event data, the process partitions the single detector ring into a set of sectors, wherein each partitioned sector includes a subset of the set of detector blocks. The process then correlates the set of detector groups to the set of sectors.

In some embodiments, the process partitions the single detector ring into a set of sectors by using one of the following schemes: (1) partitioning the single detector ring along an axial direction of the photon scanner; (2) partitioning the single detector ring along a transaxial direction of the photon scanner; and (3) partitioning the single detector ring along both the axial direction and the transaxial direction of the photon scanner.

In some embodiments, the process generates the singles-rate time series for a given channel of raw singles-event data by: (1) determining the predetermined temporal resolution based on one or more characteristic signal frequencies or periods associated with the one or more physiological motions; and (2) summing the given channel of raw singles-event data in each predetermined temporal resolution to generate a sequence of singles count values at the predetermined temporal resolution.

In some embodiments, the predetermined temporal resolution is significantly smaller than each of the one or more characteristic signal periods. However, the predetermined temporal resolution is significantly larger than a singles-event recording resolution used to generate the multiple channels of raw singles-event data.

In some embodiments, the process obtains the overall singles-rate time series by: (1) normalizing each singles-rate time series in the set of singles-rate time series; (2) assigning a weight to each singles-rate time series in the set of singles-rate time series based on a signal quality of the given singles-rate time series; and (3) computing a weighted sum of the set of singles-rate time series using the set of assigned weights to obtain the overall singles-rate time series. Note that the overall singles-rate time series has a significantly higher signal to noise ratio (SNR) than a SNR associated with each individual singles-rate time series in the set of singles-rate time series.

In some embodiments, prior to computing the weighted sum of the set of singles-rate time series, the process phase-aligns the set of singles-rate time series by: (1) identifying, in the set of singles-rate time series, each phase-inverted singles-rate time series; and (2) performing a phase-inversion on each identified phase-inverted singles-rate time series.

In some embodiments, the process assigns the weight to the given singles-rate time series based by: (1) assigning a higher weight value to the given singles-rate time series if the given singles-rate time series is associated with a higher SNR; and (2) assigning a lower weight value to the given singles-rate time series if the given singles-rate time series is associated with a lower SNR.

In some embodiments, processing the weighted-sum singles-rate time series to extract in real-time one or more motion signals further includes the steps of: (1) identifying a characteristic frequency for each of the one or more physiological motions; (2) performing a frequency domain analysis on the overall singles-rate time series to obtain a corresponding power spectrum; (3) filtering the power spectrum around the identified characteristic frequencies to obtain one or more filtered frequency-domain signals corresponding to the one or more physiological motions; and (4) converting the one or more filtered frequency-domain signals into the one or more real-time motion signals in the time domain.

In some embodiments, each of the one or more motion signals is a periodic time series, and a given value of the periodic time series at a given time is proportional to the amplitude of the corresponding physiological motion at the given time.

In some embodiments, the process generates the overall singles-rate time series by combining the set of singles-rate time series in a manner to maximize an SNR for the overall singles-rate time series.

In some embodiments, the process further includes using an extracted real-time motion signal as a gating signal to reconstruct a set of real-time dynamic photon scan images corresponding to a set of different phases of the corresponding physiological motion.

In some embodiments, the photon scanner is one of: (1) a positron emission tomography (PET) scanner; (2) a single photon emission computed tomography (SPECT) scanner; (3) a photon-counting computed tomography (PCCT) scanner; (4) an X-ray CT; and (5) a planar/curved gamma camera.

In some embodiments, the PET scanner includes an extended axial field of view (FOV) to achieve an increased SNR in the generated singles-rate time series.

In some embodiments, the one or more physiological motions of the live subject includes at least one of: (1) a cardiac motion of the heart of the live subject; (2) a respiratory motion of the lung of the live subject; (3) a periodic motion of a non-cardio-respiratory organ of the live subject; and (4) a gross motion of the live subject.

In some embodiments, using the raw singles-event data to perform real-time subject-motion tracking takes place prior to performing coincidence-event sorting.

In some embodiments, the process extracts the real-time one or more motion signals without using any external monitor device, such as an electrocardiogram (EKG or ECG), a breathing belt, or an optical/video tracker.

In another aspect, a photon scanner is disclosed. This photon scanner can include (1) at least one detector array or detector ring; (2) one or more data processors coupled to the at least one detector array or detector ring; and (3) a memory coupled to the one or more data processors. The memory stores instructions that, when executed by the one or more data processors, cause the photon scanner to perform real-time subject-motion-tracking during photon imaging by performing the steps of: (1) receiving multiple channels of raw singles-event data from a set of detector groups of the at least one detector array or detector ring while scanning a live subject; (2) for each received channel of raw singles-event data, generating a singles-rate time series based on a predetermined temporal resolution; (3) combining the set of singles-rate time series corresponding to the set of detector groups to generate an overall singles-rate time series; and (4) processing the weighted-sum singles-rate time series to extract in real-time one or more motion signals corresponding to one or more physiological motions of the live subject while the live subject is being scanned.

In some embodiments, the disclosed photon scanner is one of: (1) a positron emission tomography (PET) scanner; (2) a single photon emission computed tomography (SPECT) scanner; (3) a photon-counting computed tomography (PCCT) scanner; (4) an X-ray CT; and (5) a planar/curved gamma camera.

In some embodiments, the PET scanner includes an extended FOV to achieve an increased SNR in the generated singles-rate time series.

In yet another aspect, a process for performing motion-free reconstruction of PET images on a PET scanner is disclosed. During operation, the process begins by receiving multiple channels of raw singles-event data from a set of detector groups of the PET scanner while scanning a live subject. Next, for each received channel of raw singles-event data, the process generates a singles-rate time series based on a predetermined temporal resolution. The process then combines the set of singles-rate time series corresponding to the set of detector groups to generate an overall singles-rate time series. The process next processes the weighted-sum singles-rate time series to extract the real-time motion signal corresponding to a physiological motion of the live subject while the live subject is being scanned. The process subsequently uses the extracted real-time motion signal as a gating signal to reconstruct a set of real-time dynamic PET scan images corresponding to a set of different phases of the corresponding physiological motion.

In some embodiments, the real-time motion signal is a periodic time series, and a given value of the periodic time series at a given time is proportional to the amplitude of the corresponding physiological motion at the given time.

In some embodiments, the process generates the overall singles-rate time series by combining the set of singles-rate time series in a manner to maximize an SNR for the overall singles-rate time series.

In some embodiments, the one or more physiological motions of the live subject includes at least one of: (1) a cardiac motion of the heart of the live subject; (2) a respiratory motion of the lung of the live subject; (3) a periodic motion of a non-cardio-respiratory organ of the live subject; and (4) a gross motion of the live subject.

DETAILED DESCRIPTION

Figure 1:
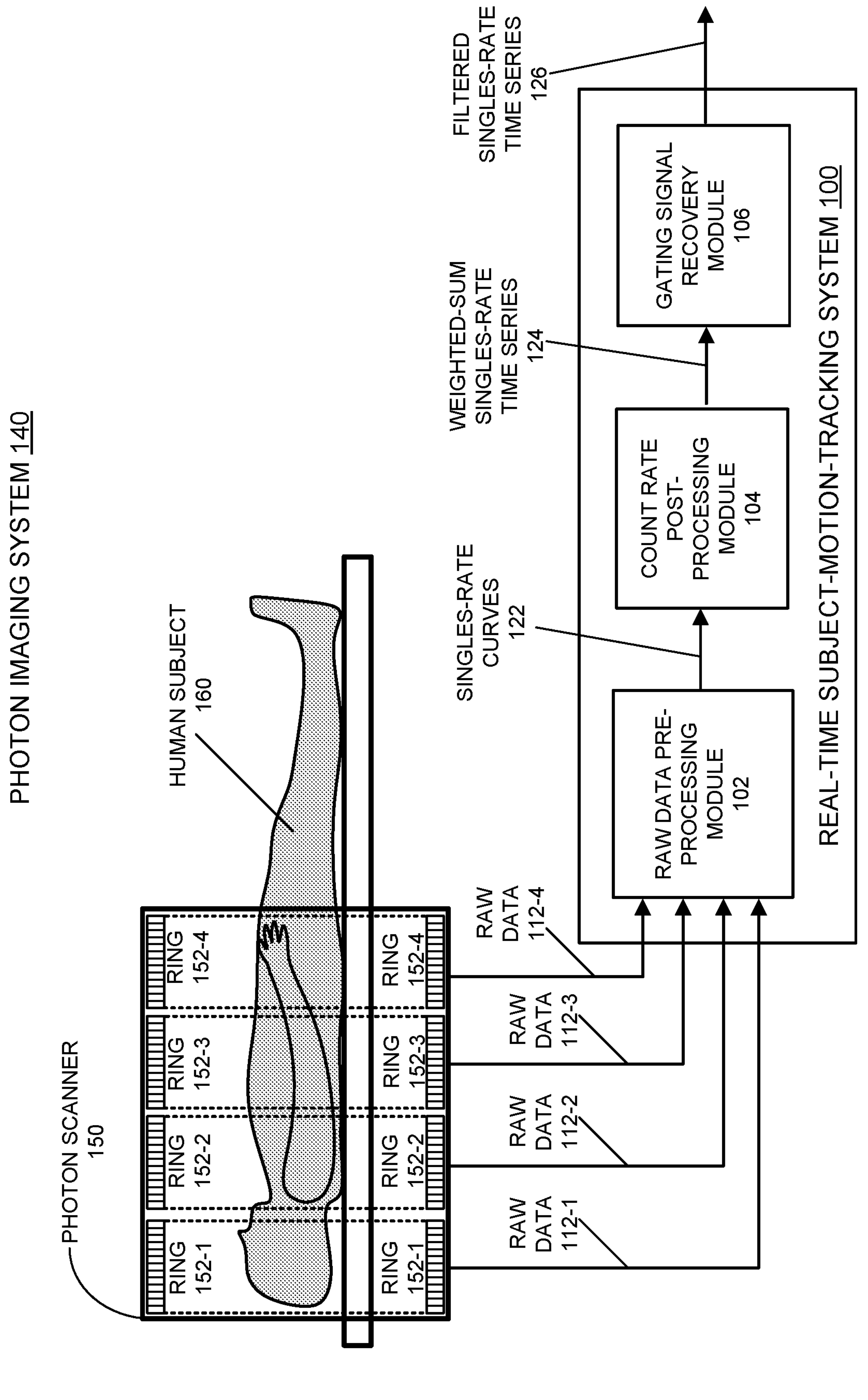
FIG. 1 illustrates a block diagram of the disclosed real-time subject-motion-tracking system for extracting real-time subject motion signals during photon imaging, in accordance with the disclosed embodiments.

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Terminology

Throughout this patent disclosure, the terms "physiological motion," "subject motion," and "motion" are used interchangeably to refer to a form of movement of a particular body part of a live subject undergoing a photon-imaging scan.

Overview

Various techniques are disclosed for performing real-time subject-motion-tracking during photon (e.g., PET and SPECT) imaging by applying various data processing techniques on raw photon-events data generated by photon imaging (PET and SPECT) scanners. Unlike existing data-driven motion-correction techniques through either the reconstructed images-based or the projection-based gating methods (e.g., listmode or sinogram, centroid-of-distribution or COD, PCA, etc.), the disclosed techniques utilize the intrinsic real-time photon (in particular the singles) counting capabilities in these photon imaging systems, and are designed to identify and extract gating signals of the subject motions (e.g., cardiac and respiratory motions) from the raw photon-events data with high temporal resolutions. The disclosed real-time motion-tracking techniques can be integrated with existing photon imaging systems as a built-in software tool or a part of the data acquisition hardware to extract cardio-respiratory motion information directly from the raw scanner data.

More specifically, the disclosed motion-tracking techniques can first construct time-count curves (TCCs) or count-rate time series (CRTSs) (e.g., the rate of singles or coincidences events as a function of time for PET scanners, or rate of singles events as a function of time for SPECT scanners) directly from raw photon-counting data. The motion-tracking techniques subsequently recover gating signals of the target motions (e.g., the cardiac motion and/or the respiratory motion) from these events-rate time series. In some embodiments, the disclosed motion-tracking techniques are configured to extract a periodic time series signal associated with a tracked motion of a large organ (e.g., the heart beating or the lung breathing) from the corresponding TCCs/CRTSs. Specifically, frequency domain analyses and band-pass filtering can be applied to these TCCs/CRTSs based on the characteristic motion periods/frequencies of the large organ. The recovered periodic temporal signal can then serve as the gating signal for reconstructing the motion-free dynamic photon (e.g., PET) scanning images.

Note that the disclosed motion-tracking techniques provide significant advantages over the existing data-driven motion-tracking techniques because of the ability to extract motion (e.g., cardio-respiratory) signals in real-time. Moreover, the disclosed motion-tracking techniques can potentially replace conventional external monitoring techniques for cardiac motions, such as electrocardiogram (EKG or ECG), as well as for respiratory motions, such as breathing belts or optical markers/video trackers. The disclosed real-time motion-tracking techniques can be integrated into existing photon imaging systems as a part of the data-processing software or a part of the data acquisition hardware. Due to the similar operating principles of photon-counting related systems, the disclosed motion-tracking techniques are not only applicable to PET and SPECT imaging systems, but can be integrated with other types of high-energy photon imaging modalities, such as photon-counting computed tomography (PCCT), X-ray CT, planar gamma camera, among others.

The disclosed motion-tracking techniques have demonstrated both high effectiveness and high accuracy in tracking cardio-respiratory motion signals in a wide range of human subjects. Compared with the conventional data-driven techniques based on list-mode events, such as the aforementioned COD technique, the disclosed techniques can directly extract the cardio-respiratory gating information from the count-rate time series without any computation in mapping between the projection space and the image space. The disclosed motion-tracking techniques allow the cardio-respiratory motion information from fast/dynamic PET scans to be extracted directly from the intrinsic singles counts prior to the coincidence sorting procedure. The disclosed motion-tracking techniques alleviate the need for post-processing procedures using existing projection-domain or image-domain techniques.

Due to the flexibility of photon counting by PET or SPECT, the disclosed singles-based motion-tracking techniques can be conveniently integrated into the corresponding photon imaging system by way of either a built-in software module, a part of the overall data-processing software, or a part of the acquisition hardware to generate the cardio-respiratory gating signals in real-time during photon imaging, which is not possible from the existing data-driven techniques. Due to the inherent flexibility, each disclosed motion-tracking technique can be an excellent substitution for common external motion-tracking monitors (e.g., breathing belt or EKG), and can play an essential role in detecting both cardiac beating and respiratory changes for accurate quantitative analysis.

Another aspect of this disclosure is to provide a singles-map estimation technique using machine learning or deep learning to predict cardiac motion signal or other weaker subject motion signals. By combining the time series of the singles maps with a machine learning or deep learning model, motion features can be identified and extracted to achieve robust motion tracking for smaller/weaker subject motion signals.

FIG. 1 illustrates a block diagram of a real-time subject-motion-tracking system 100 (also referred to as "motion-tracking system 100" or "system 100" hereinafter) for extracting real-time subject motion signals during photon imaging in accordance with the disclosed embodiments. As can be seen in FIG. 1, real-time motion-tracking system 100 can include at least the following functional modules: (1) a raw-data pre-processing module 102; (2) a count-rate post-processing module 104; and (3) a gating signal recovery module 106, which are coupled to each other in the order shown. In various embodiments, the disclosed real-time motion-tracking system 100 is used to isolate and extract in real-time one or more gating signals associated with one or more physiological motions of the subject (e.g., a human) that occur during a photon imaging process. These physiological motions that can be isolated and extracted by the disclosed motion-tracking system 100 can include, but are not limited to, a cardiac motion of the heart of the subject, a respiratory motion of the lung of the subject, a periodic motion of another large organ other than the heart and the lung, and a gross motion (e.g., moving the body) of the subject. Generally speaking, the tracked motions (also referred to as "target motions") of the disclosed motion-tracking system 100 are associated with the large organs such as the heart and the lung. Moreover, each target motion of the disclosed motion-tracking system 100 is typically periodic so that the target motion can be characterized with a characteristic period/frequency.

As can be seen in FIG. 1, the disclosed real-time motion-tracking system 100 is coupled to a photon scanner 150 comprising one or more detector module rings. In various embodiments, photon scanner 150 can include, but is not limited, to a positron emission tomography (PET) scanner, a single photon emission computed tomography (SPECT) scanner, a photon-counting computed tomography (PCCT) scanner, an X-ray CT, a planar gamma camera, and other types of photon imaging scanners, among others. Note that throughout this disclosure, a PET scanner, and in particular a full-body PET scanner, will be used as the main example to demonstrate the operations and performances of the disclosed real-time motion-tracking system and techniques. However, the disclosed real-time motion-tracking system and techniques are generally applicable to a wide range of photon imaging systems used for scanning live subjects in either clinical or preclinical applications (some of which are listed above), and therefore are not limited to the scope of PET scanners.

As can be further observed in FIG. 1, photon scanner 150 includes a set of detector blocks or module rings 152 (also referred to as "detector rings" or simply "rings" hereinafter) that are arranged along an axial/horizontal direction of photon scanner 150, wherein each detector ring covers a limited axial field-of-view (FOV) and a different region of the human subject 160, and the combined set of detector rings provide an extended axial FOV covering a large portion of the human subject 160. Note that each detector ring in the set of detector rings can be independently coupled to the real-time motion-tracking system 100 to output the raw photon-events data recorded by a two-dimensional (2D) array of detectors within the given detector ring. This configuration allows for generating the count-rate time series independently for different axial sections of subject 160. Although 4 detector rings are shown in photon scanner 150 of FIG. 1, the disclosed real-time motion-tracking system 100 is configured to operate with any number of detector rings and process raw photon-events data generated by any number of detector rings, and therefore is not limited by a particular detector-ring configuration of photon scanner 150. For example, various examples demonstrated below include a total-body PET scanner equipped with 8 detector module unit-rings that can cover the entire human body. Moreover, the disclosed real-time motion-tracking system 100 is also fully applicable to conventional photon scanners configured with a single detector module/ring with shorter axial FOVs (e.g., <30 cm).

During operation, real-time motion-tracking system 100 can begin when raw-data pre-processing module 102 receives multiple channels of raw recorded data 112-1 to 112-4 outputted from the set of detector rings 152-1 to 152-4 when photon scanner 150 is performing scans on human subject 160. Generally speaking, each channel of raw recorded data 112-1 to 112-4 includes raw list-mode data files, wherein each list-mode data file lists the values of the measured singles-events by the corresponding detectors within the corresponding detector ring 152-1 to 152-4. In some embodiments, the raw recorded data outputted from each detector ring is composed of a sequence of 2D spatial maps of the measured singles-events rate (also referred to as "singles-rate maps") corresponding to the 2D array of detectors within the detector ring, wherein each singles map is generated at a given temporal resolution on the order of 1-millisecond. Note that counting singles-events is an intrinsic capability of the photon scanner 150 hardware. By directly receiving and processing recorded singles data, real-time motion-tracking system 100 does not need to perform additional coincidence sorting to generate secondary raw acquisition files for real-time motion tracking.

As mentioned above, real-time motion-tracking system 100 can be integrated with photon scanner 150 to form an overall photon imaging system 140, wherein real-time motion-tracking system 100 can be implemented as either a built-in software module of photon imaging system 140, a part of the overall data-processing software of photon imaging system 140, or a part of the acquisition hardware of photon imaging system 140.

Note that in cases when a photon scanner contains just a single detector module/ring instead of multiple rings as shown in FIG. 1, the blocks of detectors within the single detector module/ring can be first partitioned into a set of subgroups/sectors of detectors, wherein the partition can be performed along either or both the axial direction and the transaxial direction of the single detector module/ring. Moreover, the partition scheme of the single detector module/ring along either the axial direction or the angular direction can be equal-sized partitions or uneven-sized partitions. For example, when partitioning the single detector module/ring around the transaxial direction, smaller partition sizes can be used in the regions of the single detector module/ring that are closer to the heart and/or the lung (or torso) region, whereas larger partition sizes can be used in the regions of the single detector module/ring that are further away from the heart and/or the lung (or torso) region. Once the single detector module/ring of the photon scanner is partitioned into multiple detector sectors, raw-data pre-processing module 102 can receive multiple channels of raw singles data corresponding to the multiple partitioned detector sectors when the photon scanner is performing scans on human subject 160. Moreover, the additional functionalities of motion-tracking system 100 described below, such as generating a set of singles-rate time series and combining the set of singles-rate time series can be equally applicable to the received multiple channels of raw singles data corresponding to the multiple detector sectors.

In various embodiments, raw-data pre-processing module 102 is configured to generate a time-series of the singles rate (also referred to as a "singles-rate time series") from each channel of raw singles data 112 based on a predetermined temporal resolution/timing window corresponding to a target motion. This means that the raw singles data for each detector ring/sector, which were recorded at ~1-millisecond intervals, are summed/combined based on the predetermined temporal resolution to generate a sequence of singles count values at the predetermined temporal resolution. More specifically, this predetermined temporal resolution may be determined based on the characteristic periods/frequencies of one or more subject motions. For example, for cardiac motion tracking, the characteristic period/frequency of the target motion is the result of the heartbeat rate, which is generally between 50 beats per minute (BPM) and 120 BPM. It has been observed that using a temporal resolution of 0.1 s to generate the singles-rate time series for the cardiac motion tracking is generally sufficient to achieve the required signal resolution and signal-to-noise ratio (SNR). However, in other embodiments of raw-data pre-processing module 102, the temporal resolution greater than or less than 0.1-sec (or simply "0.1 s") can also be used for tracking cardiac motions. As shown in FIG. 1, raw-data pre-processing module 102 generates as output a set of the singles-rate time-series, such as a set of singles-rate time series 122 associated with the predetermined temporal resolution (e.g., 0.1 s).

Further referring to FIG. 1, count-rate post-processing module 104 in motion-tracking system 100 receives the set of singles-rate time series 122 and is configured to combine the set of singles-rate time series 122 corresponding to the set of detector rings/sectors in a manner to significantly improve or maximize the signal-to-noise ratio (SNR) for the tracked motions. In some embodiments, count-rate post-processing module 104 is configured to combine the set of singles-rate time series 122 by computing a weighted sum of the set of singles-rate time series 122, wherein a given weight for a given singles-rate time series in the set of singles-rate time series 122 is determined based on the quality of the SNR of the given singles-rate time series. In other words, a significantly higher weight is provided to a given singles-rate time series 122 associated with a higher SNR, whereas a significantly lower weight is provided to a given singles-rate time series 122 associated with a lower SNR. In some embodiments, count-rate post-processing module 104 is further configured to identify each and every phase-inverted singles-rate curve in the set of singles-rate time series 122, and invert each identified phase-inverted singles-rate curve before combining such phase-inverted singles-rate curve with other singles-rate time series. By doing so, potential phase cancellation effect when combining the set of singles-rate time series 122 can be eliminated. As shown in FIG. 1, count-rate post-processing module 104 outputs a weighted-sum singles-rate time series 124 that has significantly higher SNR than the individual singles-rate time series in the set of singles-rate time series 122.

Gating signal recovery module 106 in motion-tracking system 100 receives the weighted-sum singles-rate time series 124 and performs a number of frequency domain analyses to extract one or more target motion signals from the weighted-sum singles-rate time series 124, thereby recovering the gating signals for photon scanner 150. In some embodiments, gating signal recovery module 106 is configured to compute the signal power spectrum of the weighted-sum singles-rate time series 124 in the frequency domain. Signal recovery module 106 then applies one or more band-pass filters to the computed signal power spectrum to filter out one or more portions of the signal power spectrum corresponding to one or more target subject motions. As mentioned above, each target motion, such as cardiac motion or respiratory motion, can have characteristic periods/frequencies as a result of the corresponding physiological process. Hence, after band pass filtering, periodic motion signals corresponding to the target motion can be isolated and extracted. Note that by applying different band-pass filters to different portions of the signal power spectrum corresponding to different types of physiological motions, different motion signals corresponding to different target subject motions can be isolated and extracted. Gating signal recovery module 106 subsequently computes and outputs one or more filtered singles-rate time series 126 corresponding to one or more isolated subject motions as the outputs of real-time motion-tracking system 100. Subsequently, the filtered singles-rate time series 126 can be used as the recovered gating signals for reconstructing motion-free photon scanning images for the human subject 160.

Note that the ability of motion-tracking system 100 to perform real-time subject motion tracking based on the intrinsic singles counts is rooted in the observation that if a pronounced organ or body movement occurred during a photon imaging process, such as a PET scan, the changing spatial distribution of the scanned subject would cause significant amounts of singles-rate fluctuation and spatial-detection sensitivity variation. Moreover, the inherent simplicity in data acquisitions and low computational burden in data processing of the disclosed singles-driven motion-tracking techniques allow for extracting motion-tracking signals in real-time during a photon-imaging scan, such as a PET scan, without requiring any additional external monitoring means. Compared to acquiring true prompts (i.e., coincidence events) rate by processing list-mode or sinogram files, collecting singles rate in detectors or detector blocks requires significantly less time (close to being instantaneous) and significantly less memory. Furthermore, the disclosed singles-driven motion-tracking techniques and system have significantly higher sensitivity and reliability than coincidence-driven techniques because the typical singles rate are significantly higher (e.g., >10×) than the coincidence event rate.

Real-Time Motion Tracking in Positron Emission Tomography (PET)

Among different types of photon scanners, positron emission tomography (PET) is a highly sensitive imaging modality broadly used in oncology, cardiology, and neurology, with the ability to observe molecular-level biochemical and physiological process inside a living subject through the injection of radio-labeled tracers. In order to accurately pinpoint and quantitate specific pathways in various diseases, there is growing demand for technical improvements to optimize the performance of PET. Although state-of-the-art PET scanners are able to offer images with high spatial resolutions, the inevitable artifacts resulting from subject motions (e.g., cardiac motion, respiratory motion, or gross body motion) can potentially lead to inaccurate quantification and reduced detection of clinically relevant features, leading to a negative influence on diagnosis and treatment. Unlike the essential physics compensations that are automatically implemented as corrections in each PET scanner, subject-motion correction is not routinely performed in regular PET imaging procedures despite the large amount of motion during a clinical PET scan, which can be contributed to the complexity of the existing motion-tracking techniques.

However, subject motion-induced artifacts during PET scans have become a major degrading factor that can severely reduce the accuracy of tracer assay analysis and disease stage diagnosis. This detection-accuracy problem is particularly acute for cancer patients, because 90% of PET oncology cases focus on detection of tumors in the chest or abdomen region, which are also the sources of the most significant subject motions. It has been demonstrated that respiratory motion can result in organs and lesions being displaced by a remarkable range of 5 mm to 30 mm, which causes uncertain lesion detection and misrepresentation of disease stage. Similarly, the base of the heart typically moves by a range of 9 mm to 14 mm toward the apex during quasiperiodic beating, and the myocardial walls thicken from approximately 10 mm to 15 mm between the end-diastole and end-systole. These unavoidable cardiac movements introduce notable visual and quantitative degradations in cardiac PET imaging. In case of dynamic studies, the estimate of perfusion and metabolic parameters, such as coronary flow reserve (CFR), myocardial blood flow (MBF), metabolic rate of glucose (MRglu) and $^{18}$F-FDG net uptake rate (Ki), can shift up to 18% due to these undesirable motion-induced artifacts.

The disclosed singles-driven motion-tracking techniques, when integrated with PET scanners can achieve real-time cardio-respiratory motion tracking, which in turn enables fast dynamic motion-free PET imaging. As mentioned above, the real-time nature of the disclosed motion-tracking techniques is enabled by the intrinsic capability of instant singles counting in PET hardware without the need for the time-consuming coincidence sorting procedure to generate secondary raw acquisition files. Compared to the existing data-driven motion correction approaches, the disclosed techniques can extract real-time motion information and recover gating signals from both static and dynamic PET imaging.

The principle of PET imaging is to record 511 keV photons and track the trajectory of annihilated events from the uptake radiotracer. The raw recorded singles events are acquired and then the coincidence electronics discriminate and sort two qualified singles into one coincidence event (also referred to as a "prompt"), which can be a true, scattered or random coincidence. Previously, singles-count rates have been mostly used to characterize the performance of PET systems and to estimate the random coincidence rate and dead-time. As will be demonstrated further below, motion-tracking techniques provided herein are based on the observation that singles rates contain statistically reliable signals that correlate to the motions of the patient's internal organs.

Figure 2B:
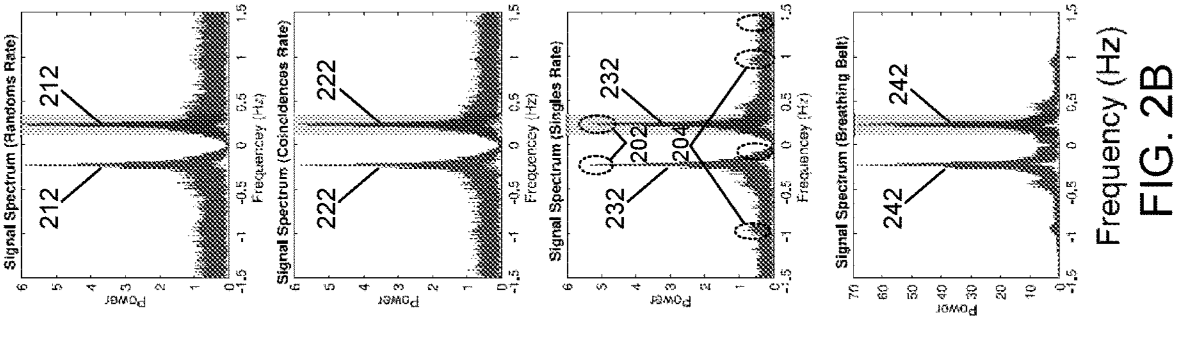
FIG. 2B shows four power spectra which correspond to the four time-series signals in FIG. 2A, in accordance with the disclosed embodiments.
Figure 2A:
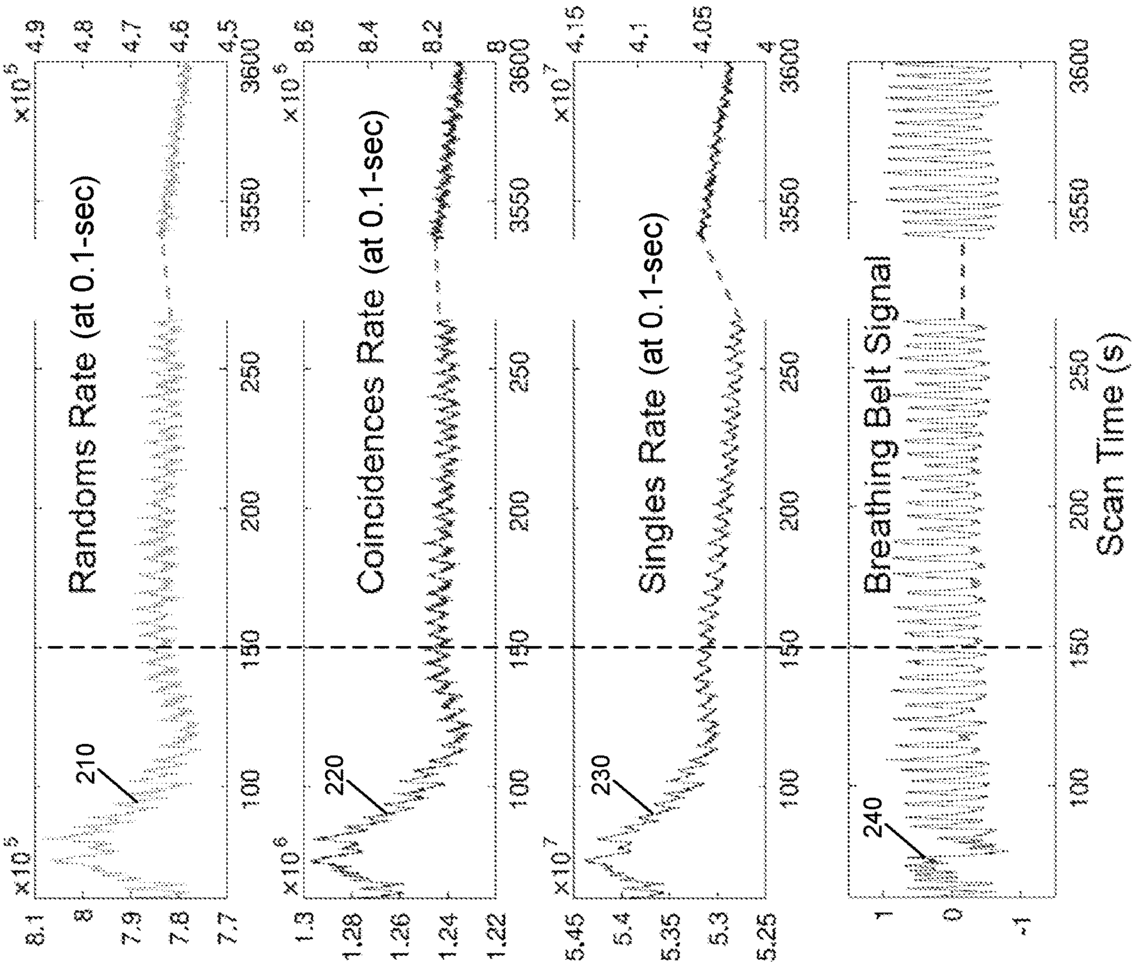
FIG. 2A shows various count-rate time series at 0.1 s temporal resolution, including a delayed-randoms-rate time series, a coincidence-prompts-rate time series, and a singles-rate time series generated from the raw data of 1-hour dynamic $^{18}$F-FDG human scan on a uEXPLORER™ PET/CT scanner with a simultaneously measured breathing belt signal as the reference, in accordance with the disclosed embodiments.

The effectiveness of real-time motion-tracking system 100 was tested on a one-hour total-body dynamic PET scan acquired during and following an intravenous injection of 10 mCi of $^{18}$F-FDG. FIG. 2A shows various count-rate time series at 0.1 s temporal resolution, including a delayed-randoms-rate time series 210, a coincidence-prompts-rate time series 220, and a singles-rate time series 230 generated from the raw data of 1-hour dynamic $^{18}$F-FDG human scan on an uEXPLORER™ PET/CT scanner with a simultaneously measured breathing belt signal 240 as the reference, in accordance with the disclosed embodiments. Note that all data points in the three count-rate time series 210-230 have the unit of count-per-0.1-second, which means that the data are aggregated over 0.1-second time intervals.

Although all three count-rate time series show a similar long-term trend over the 1-hour range, they differ a great deal in signal amplitude. For example, at t=150 sec, the singles rate is almost 45 time the coincidences rate and 67 time the randoms rate. Indeed, it has been established that the singles rate represents a far greater statistical count level than that of the coincidence rate, typically by a factor of over 10× in total-body PET. Consequently, using the singles rate for real-time motion-tracking is preferred over other types of count rate such as the coincidences rate or the randoms rate, because the significant higher statistical counts in the singles rate allows for increased temporal resolution for detecting and correcting the target subject motions. However, in some embodiments, either the coincidences rate or the randoms rate may be used by real-time motion-tracking system 100 for extracting motion signals, either in place of or in combination with the singles rate. Moreover, the coincidences rate or the randoms rate may be used with a machine learning or deep learning technique to reliably predict target motion signals even when the associated SNR is significantly lower than that of the singles rate.

FIG. 2A also shows that the singles-rate time series 230 oscillates with pronounced cycles, which are visually aligned with the breathing belt signal 240. This unmistakable correlation between the time series of singles rate and the periodic motions of the lung organs is the underlying reason for using singles rate in the disclosed real-time motion-tracking techniques. FIG. 2B shows four power spectra 212-242 that correspond to the four time-series signals in FIG. 2A. The first observation from FIG. 2B is that singles-rate time series 230 has the highest SNR among the three count-rate time series 210-230. By comparing power spectra 232 and 242, the correlation is further validated that the peak frequency 202 (at ±0.24-Hz) in the singles-rate time series 230 is identical to the peak frequency in the measured breathing signal 240, which is the result of the respiratory motion. Note that even though all three power spectra 212-232 corresponding to the three count-rate time series 210-230 showed the main spectral peaks at ±0.24-Hz due to the large breathing motion, only power spectrum 232 corresponding to the singles-rate time series 230 also shows a secondary spectral peak 204 at ±0.95-Hz, which corresponds to the smaller/weaker cardiac motion. In contrast, there are no such secondary spectral peaks from the cardiac motion shown in power spectra 212 and 222 because of the much lower SNRs and high levels of noise in the corresponding count-rate time series 210 and 220.

Figure 3A:
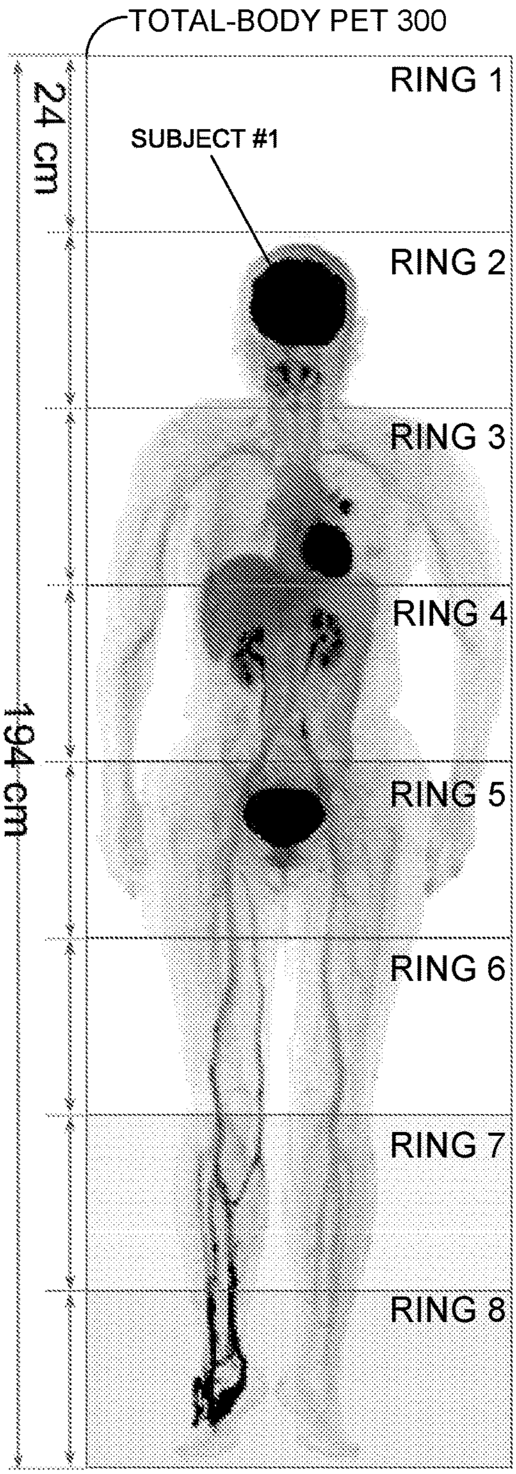
FIG. 3A illustrates the spatial arrangements of a set of 8 detector rings of a total-body PET scanner relative to a human subject, in accordance with the disclosed embodiments.

The effectiveness of singles-based motion-tracking system 100 on multiple detector rings was further tested on a 194-cm long uEXPLORER™ total-body PET/CT scanner comprises 8 PET detector rings, each of which covered an axial FOV of 24 cm. FIG. 3A illustrates the spatial arrangements of the set of 8 detector rings (Ring 1 to Ring 8) of a total-body PET scanner 300 relative to a human subject (referred to as "subject #1" below) in accordance with the disclosed embodiments. For example, Ring 2 covers the subject's head region; Ring 3 covers the subject's epigastric (chest and heart) region; Ring 4 covers the subject's umbilical (upper abdomen) region; and Ring 5 covers the subject's hypogastric (lower abdomen) region. Note that each unit ring has a length of 24 cm in the axial direction, which results in the total length of 194 cm of the total-body PET scanner 300. The raw singles dataset from the total-body PET scanner 300 was divided and combined based on a 100-millisecond temporal interval (i.e., the temporal resolution used for motion tracking) and analyzed over the 1-hour dynamic scan, which represent the fast tracer transit and tracer uptake at equilibrium status, respectively.

Figure 3B:
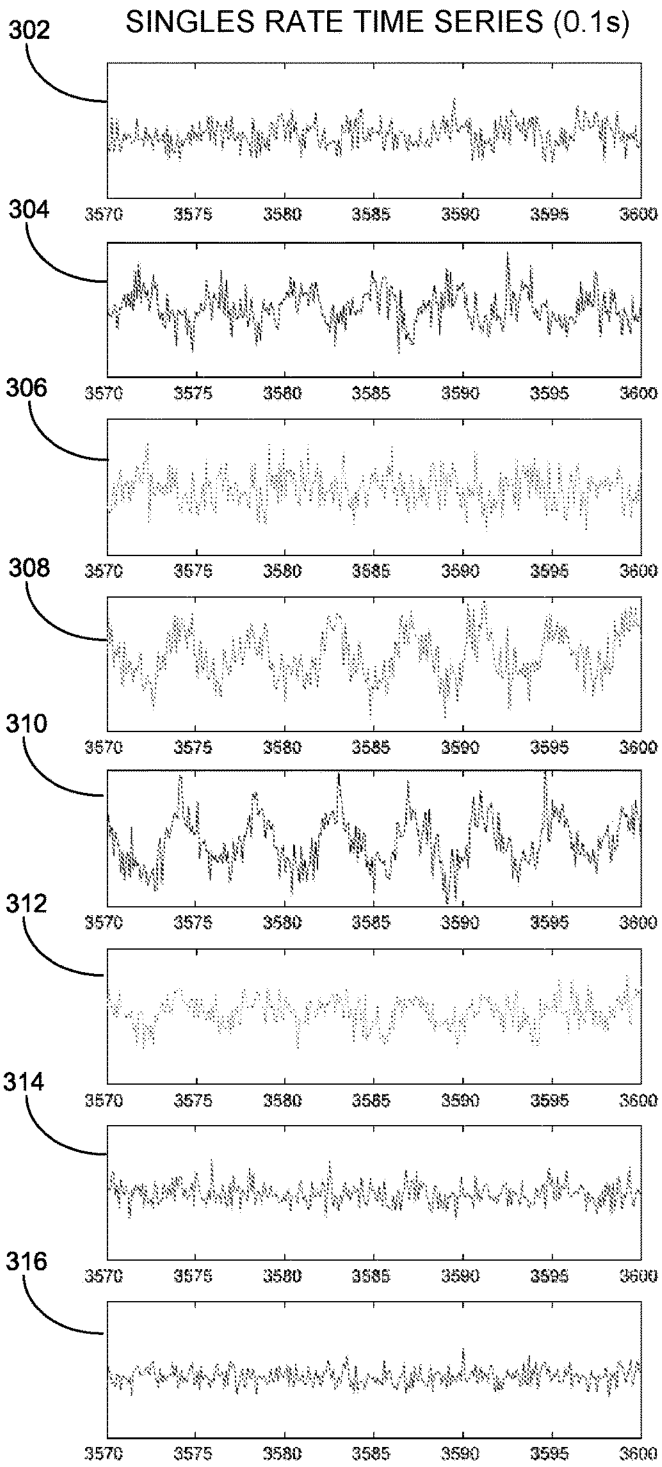
FIG. 3B shows, from top to bottom, 8 singles-rate time series at 0.1 s temporal resolution generated from raw singles data collected from the set of detector rings in FIG. 3A, in accordance with the disclosed embodiments.

FIG. 3B shows, from top to bottom, 8 singles-rate time series 302-316 at 0.1 s temporal resolution generated from raw singles data collected from the set of unit rings 1-8 in FIG. 3A in accordance with the disclosed embodiments. Moreover, singles-rate time series 302-316 at 0.1-sec temporal resolution are generated from raw singles data from total-body PET 300 when scanning subject #1 with normal respiratory motion (i.e., normal breathing patterns). It can be clearly observed that singles-rate time series 308 and 310 corresponding to Ring 4 and Ring 5 over and around the abdominal region provide the strongest periodic respiratory motion signals with substantially identical phase relationships. In contrast, singles-rate time series 304 corresponding to Ring 2 covering the subject's brain provides a relatively strong respiratory motion signal but an inverse phase relationship with respect to other rings covering regions below the lung. Note that the respiration signal cannot be clearly identified in singles-rate time series 306 from Ring 3, most likely due to the phase cancellation effect between the signals from the liver and heart. Note also that the significant variations in signal strength levels of different PET rings and inconsistency in phase relationships suggest that directly summing the set of singles count-rate time series 302-316 would not provide a desirable SNR to extract the respiratory signals.

Figures 4A, 4B:
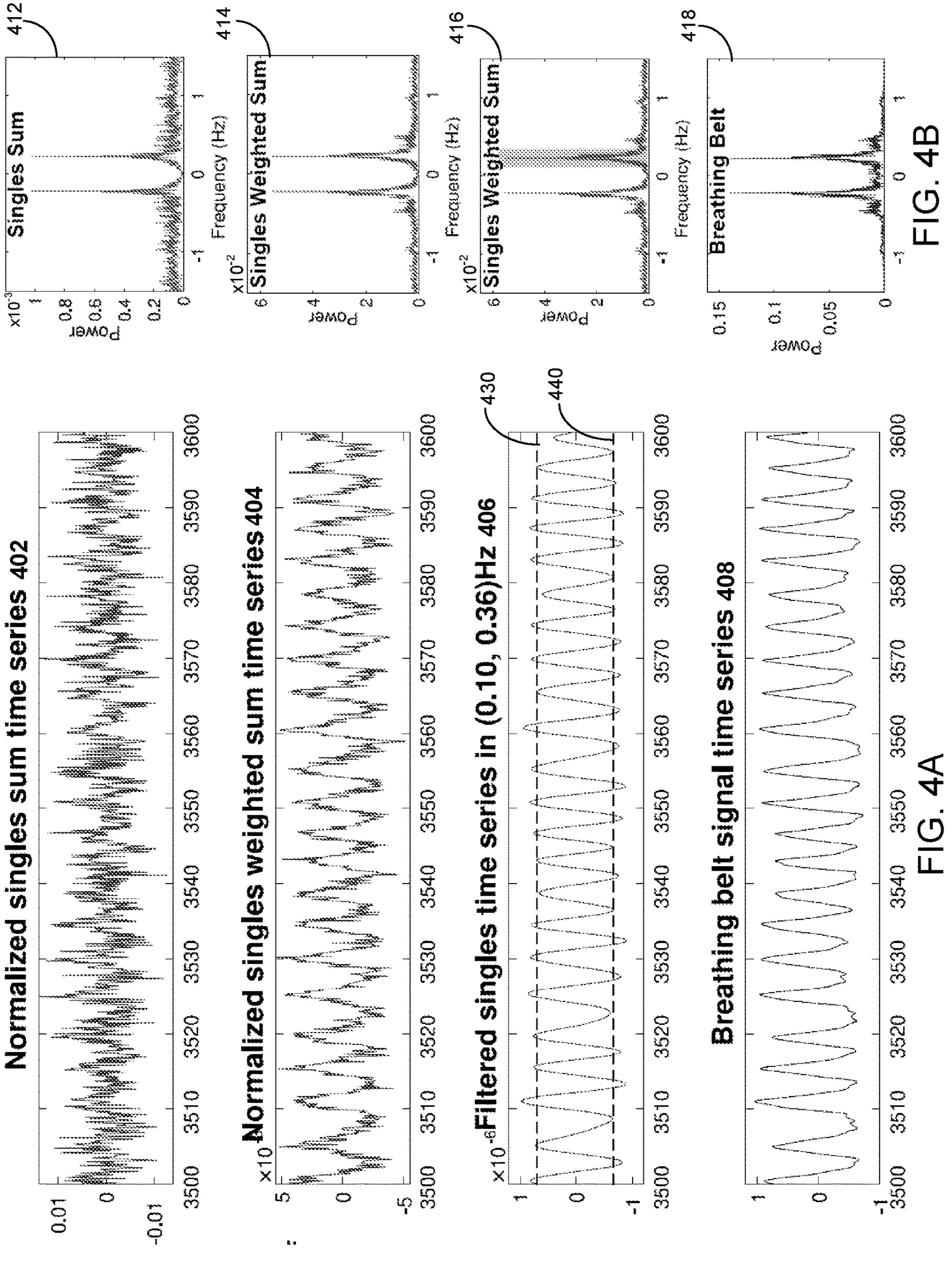
FIG. 4A illustrates the data processing steps of extracting respiratory motion signal for subject #1 from the set of singles-rate time series in FIG. 3B using the real-time motion-tracking techniques described in conjunction with FIG. 1, in accordance with the disclosed embodiments.
FIG. 4B shows four power spectra in the frequency domain, which correspond to the four time-series signals in the time domain in FIG. 4A, in accordance with the disclosed embodiments.

FIG. 4A illustrates the data processing steps of extracting respiratory motion signal for subject #1 from the set of singles-rate time series in FIG. 3B using the real-time motion-tracking techniques described in conjunction with FIG. 1 in accordance with the disclosed embodiments. Specifically, a simple-sum time series 402 in FIG. 4A shows the normalized sum of the set of singles-rate time series 302-316 without performing the above-described SNR enhancing techniques (e.g., weighting different singles-rate time series and performing phase alignment as described in conjunction with motion-track system 100 in FIG. 1). The only preprocessing on the set of singles-rate time series to obtain the simple-sum time series 402 is to normalize each of the set of singles-rate time series 302-316 first. Not surprisingly, simple-sum time series 402 is quite noisy with a low SNR due to the aforementioned reasons, such as the phase cancellation effect.

In contrast, a normalized weighted-sum time series 404 in FIG. 4A is obtained by performing the SNR enhancing techniques described in conjunction with count-rate post-processing module 104 in FIG. 1, including computing a weighted sum of the set of singles-rate time series 302-316 and performing necessary phase alignment. For example, higher weights are provided to those singles-rate time series within singles-rate time series 302-316 having higher SNRs. Moreover, each phase-inverted singles-rate curve within singles-rate time series 302-316 is identified and phase-corrected. As a result, normalized weighted-sum time series 404 displays prominent periodic respiratory signal patterns and significantly lower noise levels when compared with the simple-sum time series 402.

Next, a filtered singles-rate time series 406 in FIG. 4A is obtained after applying a band-pass filter with cut-off frequencies of 0.1-Hz and 0.36-Hz to the normalized weighted-sum time series 404. This filtering operation is used to remove noises higher or lower than the selected frequency range embedded in the normalized weighted-sum time series 404, which are unrelated to the respiratory motion of subject #1. As can be seen in FIG. 4A, filtered singles-rate time series 406 is a clean and smooth periodic time-series signal that represents the extracted normal respiratory motion of subject #1. FIG. 4A also shows a breathing belt time-series signal 408 obtained with an external breathing belt and used as the reference signal. It can be clearly observed that the filtered singles-rate time series 406 has an extremely high degree of agreement with breathing belt time-series signal 408. A quantitative analysis demonstrated that the filtered singles-rate time series 406 has a 98.5% match to breathing belt time-series signal 408 and a mean timing error of merely 1-ms when using time-series signal 408 as the reference signal. FIG. 4B shows four power spectra 412-418 in the frequency domain, which correspond to the four time-series signals in the time domain in FIG. 4A. It can be observed from FIG. 4B that normalized weighted-sum time series 404 has a significantly higher SNR than that of normalized simple-sum time series 402. By comparing the filter power spectrum 416 and the reference power spectrum 418, the high degree of agreement between the extracted respiratory motion signal 406 and the reference breathing belt signal 408 is again validated.

Figure 5A:
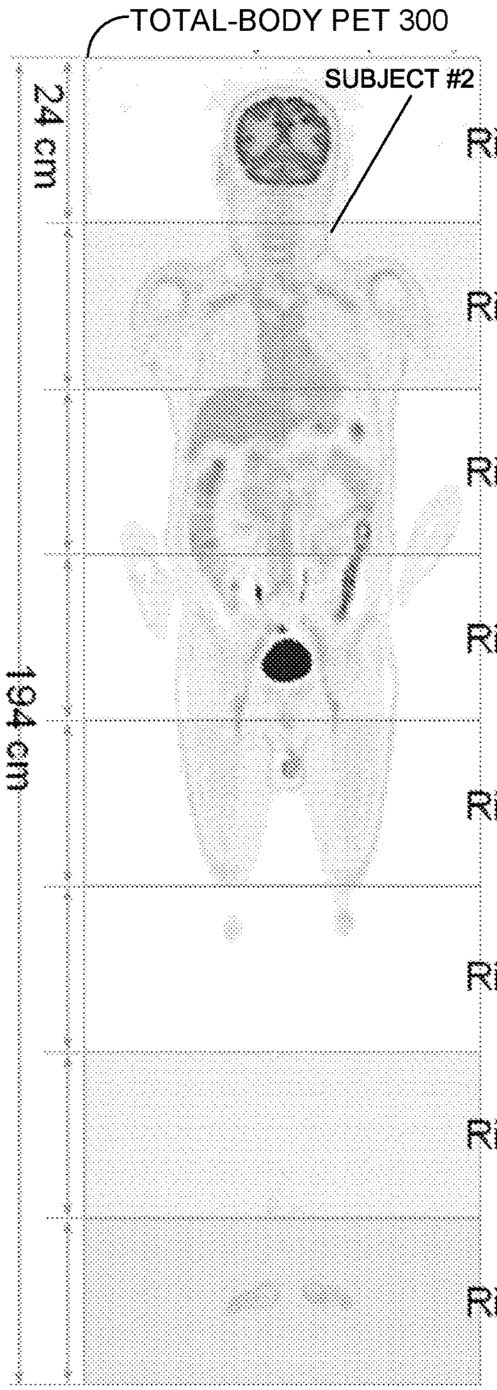
FIG. 5A illustrates the spatial arrangements of the set of 8 detector rings of the same total-body PET scanner over human subject #2, in accordance with the disclosed embodiments.
Figure 5B:
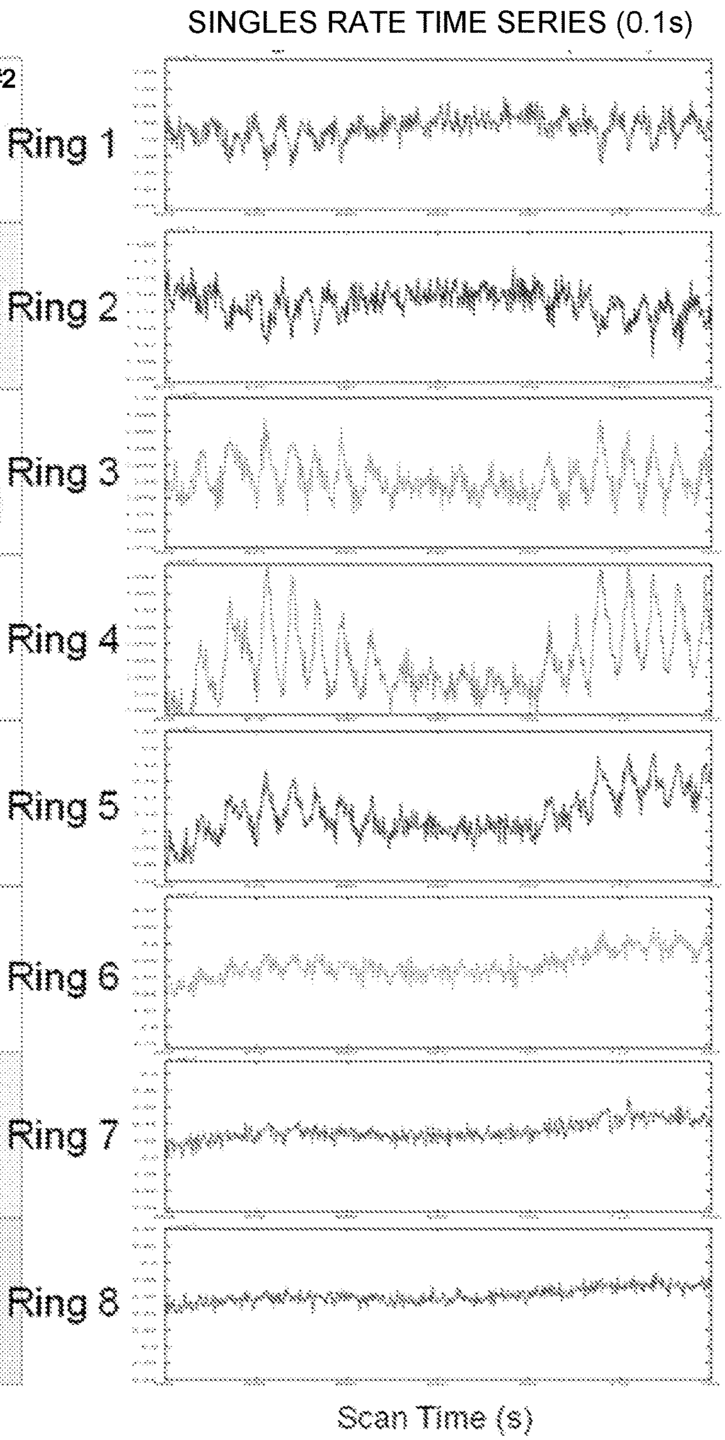
FIG. 5B shows, from top to bottom, 8 singles-rate time series at 0.1 s temporal resolution generated from the raw singles data collected from the set of 8 detector rings when scanning subject #2, in accordance with the disclosed embodiments.

The performance including the sensitivity of singles-based motion-tracking system 100 was further tested using the same 8-ring total-body PET scanner 300 on a subject #2 with irregular respiratory motion (i.e., abnormal breathing patterns). FIG. 5A illustrates the spatial arrangements of the set of 8 detector rings of total-body PET scanner 300 over human subject #2 in accordance with the disclosed embodiments. The raw singles dataset from the total-body PET scanner 300 was divided and combined based on a 100-millisecond temporal interval (i.e., the temporal resolution used for motion tracking) and analyzed over the 1-hour dynamic scan. FIG. 5B shows, from top to bottom, 8 singles-rate time series at 0.1 s temporal resolution generated from the raw singles data collected from the set of detector rings 1-8 when scanning subject #2 in accordance with the disclosed embodiments. When compared with the set of singles-rate time series in FIG. 3B corresponding to a normal respiratory motion, the singles-rate time series in FIG. 5B showed significantly higher amounts of irregularities which are indicative of underlining irregular respiratory motion.

Figure 6B:
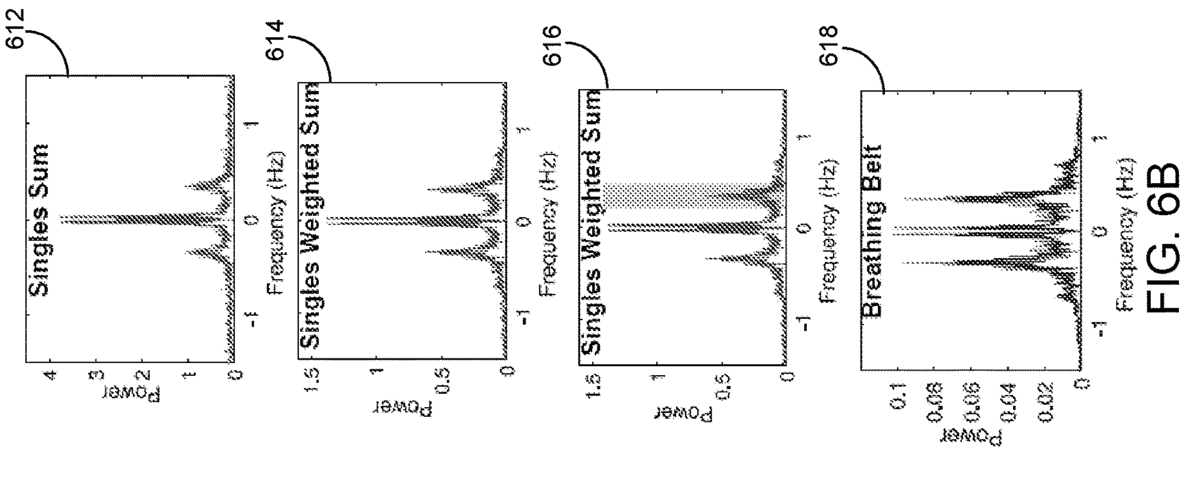
FIG. 6B shows four power spectra that correspond to the four time-series signals in FIG. 6A, in accordance with the disclosed embodiments.
Figure 6A:
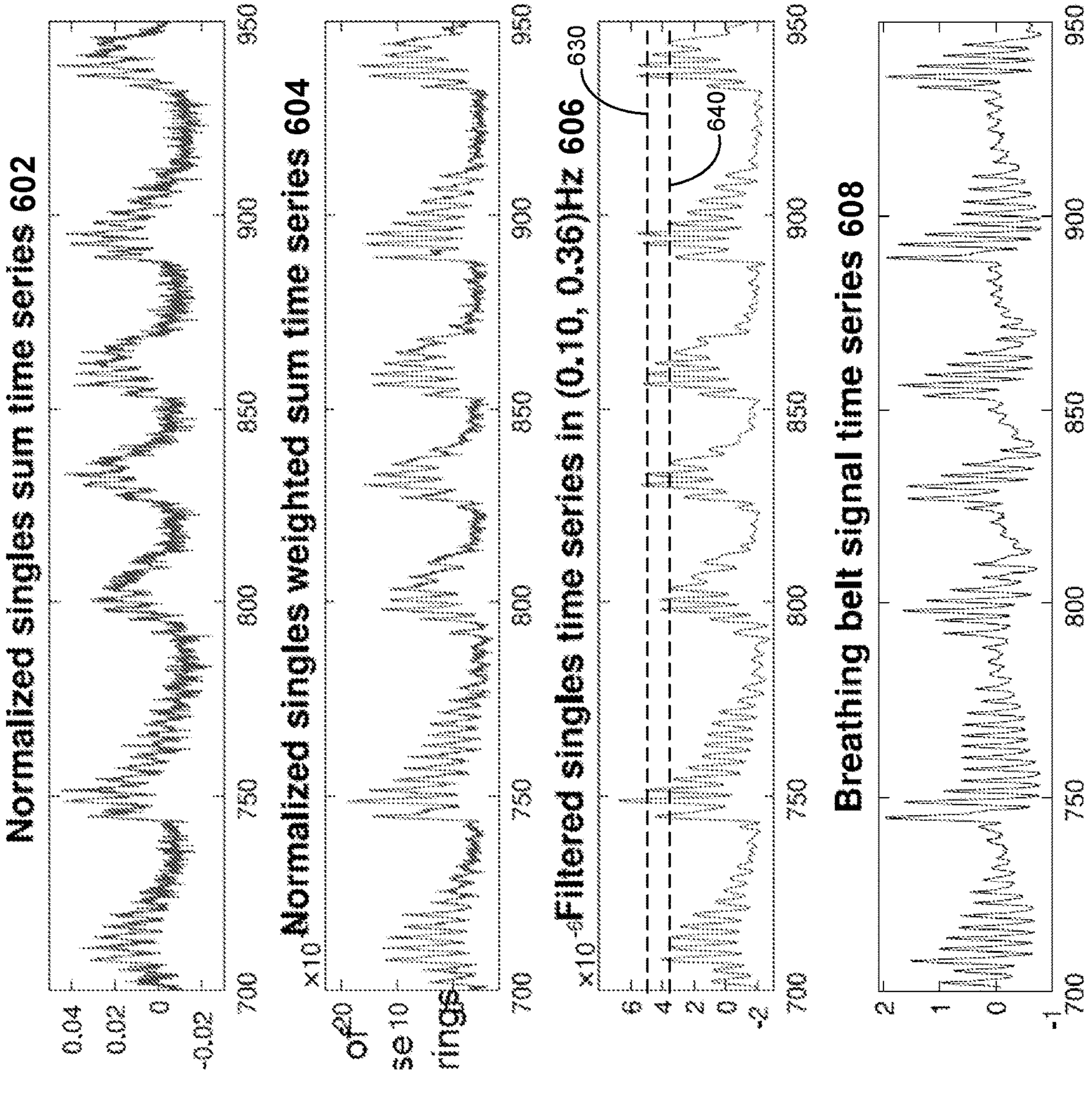
FIG. 6A illustrates the data processing step of extracting respiratory motion signal of subject #2 from the set of singles-rate time series in FIG. 5B using the real-time motion-tracking techniques described in conjunction with FIG. 1, in accordance with the disclosed embodiments.

FIG. 6A illustrates the data processing steps of extracting respiratory motion signal of subject #2 from the set of singles-rate time series in FIG. 5B using the real-time motion-tracking techniques described in conjunction with FIG. 1 in accordance with the disclosed embodiments. Again, a simple-sum time series 602 in FIG. 6A shows the normalized sum of the set of singles-rate time series in FIG. 5B without performing any SNR enhancing techniques. In contrast, a normalized weighted-sum time series 604 in FIG. 6A is obtained by performing the aforementioned SNR enhancing techniques. Not surprisingly, normalized weighted-sum time series 604 exhibits sharper respiratory signal patterns and significantly lower noise levels than the simple-sum time series 602.

Similarly, a filtered singles-rate time series 606 in FIG. 6A is obtained after applying a band-pass filter with cut-off frequencies of 0.1-Hz and 0.36-Hz to the normalized weighted-sum time series 604, to remove high frequency noises unrelated to the respiratory motion of subject #2. As can be seen in FIG. 6A, filtered singles-rate time series 606 provides a cleaner and smoother version of the weighted-sum time series 604. However, both weighted-sum time series 604 and filtered singles-rate time series 606 clearly show the irregular respiratory pattern of subject #2, which is a combination of long, deep breaths and many short breaths and shallow breaths. FIG. 6A also shows a breathing belt time-series signal 608 obtained with an external breathing belt and used as the reference signal. Again, an extremely high degree of agreement between the filtered singles-rate time series 606 and the breathing belt time-series signal 608 is achieved. A quantitative analysis demonstrated that the filtered singles-rate time series 606 has a 96% match to breathing belt time-series signal 608 and a mean timing error of about 12-ms. The singles-driven motion-track results on subject #2 have successfully isolated and extracted both of the unusually short breathes and the unusually shallow breaths. These results demonstrate the capability of the disclosed singles-driven motion-track techniques to achieve both high temporal sensitivity and high signal sensitivity.

FIG. 6B shows four power spectra 612-618, which correspond to the four time-series signals in FIG. 6A. It can be observed from FIG. 6B that normalized weighted-sum time series 604 has a significantly higher SNR than normalized simple-sum time series 602. By comparing the filter power spectrum 616 and the reference power spectrum 618 from the breathing belt, the high degree of agreement between the extracted respiratory motion signal 606 and the reference breathing belt signal 608 is again validated.

As mentioned above, one of the most direct applications of the extracted subject motion signal is to facilitate reconstructing dynamic motion-free PET images. Specifically, either a single amplitude value or a range of amplitude values within the extracted motion time-series, such as the filtered singles time series 406 or 606, can be selected as a gating signal to reconstruct a PET image corresponding to the selected amplitude value or the selected range of amplitude values. For example, referring to filtered singles time series 406 in FIG. 4A, the set of points having the same near-peak amplitude that intersects the horizontal line 430 can be used as the first gating signal to reconstruct a first PET image for subject #1 corresponding to the maximum inspiratory amplitude (i.e., when the lung expansion is near its maximum). Similarly, the set of points having the same near-minimum amplitude that intersects the horizontal line 440 can be used as the second gating signal to reconstruct a second PET image for subject #1 corresponding to the minimum expiratory amplitude (i.e., when the lung is fully relaxed). However, a gating signal can also be constructed using a range of amplitude values of the extracting motion signal. For example, referring to filtered singles time series 606 in FIG. 6A, all the data points in time series 606 that fall between horizontal line 630 and horizontal line 640 can be used as a gating signal to reconstruct a PET image for subject #2.

Figure 7A:
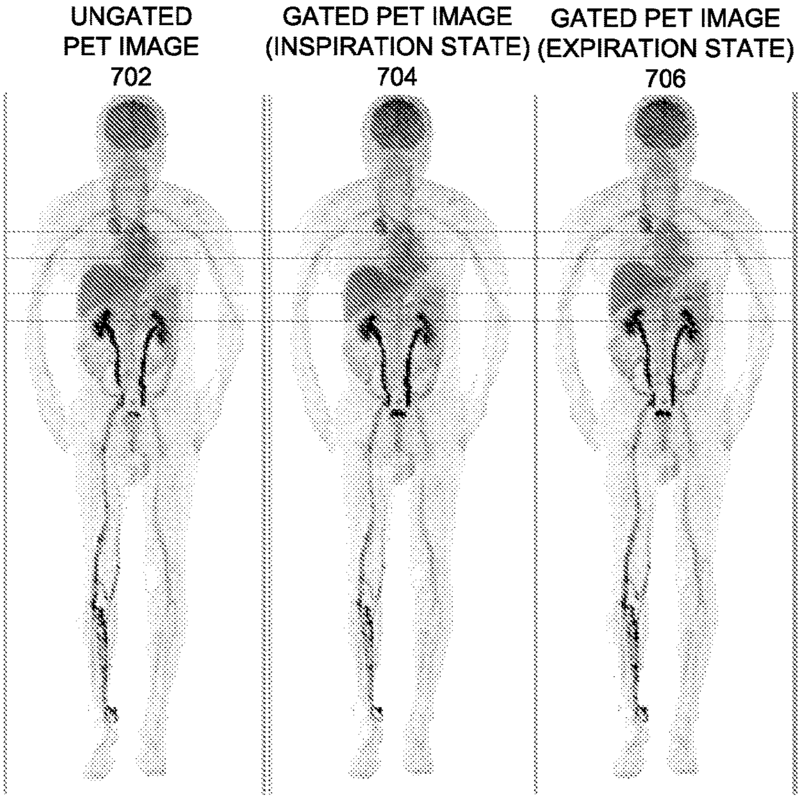
FIG. 7A shows examples of ungated reconstruction of a PET image vs. gated reconstructions of two respiratory-phased motion-free PET images of subject #2 using the extracted respiratory motion time series as gating signals, in accordance with the disclosed embodiments.
Figure 7B:
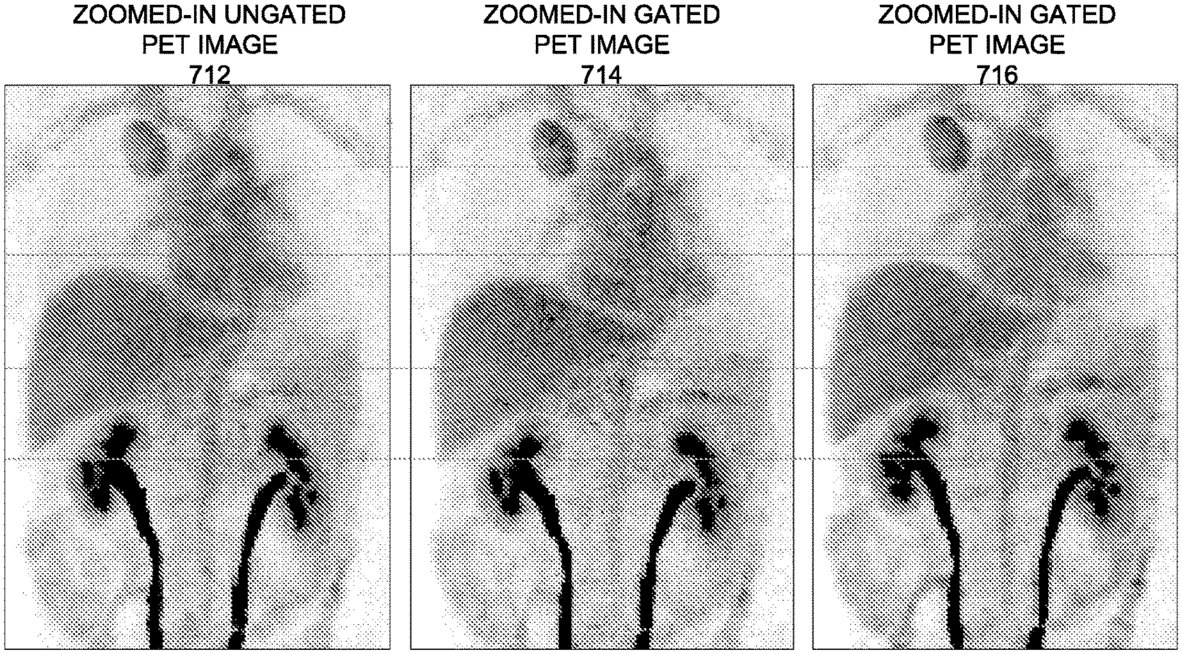
FIG. 7B provides three zoomed-in PET images of the chest region of subject #2 corresponding to the full-body PET images in FIG. 7A, respectively, in accordance with the disclosed embodiments.

FIG. 7A shows examples of ungated reconstruction of a PET image 702 vs. gated reconstructions of two respiratory-phased motion-free PET images 704 and 706 of subject #2 using the extracted respiratory motion time series 606 as gating signals in accordance with the disclosed embodiments. More specifically, PET image 702 on the left is a conventional ungated full-body PET image without subject-motion correction. In contrast, PET image 704 in the middle is a respiratory-gated full-body PET image reconstructed at an inspiration amplitude and PET image 706 on the right is a respiratory-gated full-body PET image reconstructed at an expiration amplitude, wherein both the inspiration amplitude and the expiration amplitude are selected from the recovered respiratory motion signal, i.e., singles time series 606. For the convenience of comparison, FIG. 7B provides three zoomed-in PET images 712-716 of the chest region of subject #2 corresponding to the full-body PET images 702-706 in FIG. 7A, respectively, in accordance with the disclosed embodiments.

As can be seen in PET image 702 with the help of zoom-in view 712, the ungated PET image 702 displays noticeable motion-induced blurs in the chest region, such as around the reconstructed liver and the heart. In contrast, when using the gating information from the recovered respiratory motion signals to reconstruct multiple gated PET images, the motion-induced blurs have been significantly reduced and displacements of organs corresponding to the different gating states of the respiratory cycle can be reconstructed. For example, when comparing the inspiration state PET images 704 and 714 with the expiration state PET images 706 and 716, the changing positions of the liver within the chest region can be clearly observed. Moreover, both of the gated PET images 704/714 and 706/716 demonstrate increased sharpness of the object boundaries, higher intensity levels, and better delineations between adjacent organs over the ungated PET image 702/712, which is the result of isolating the respiratory motion signals from the regular PET signals.

Figure 8:
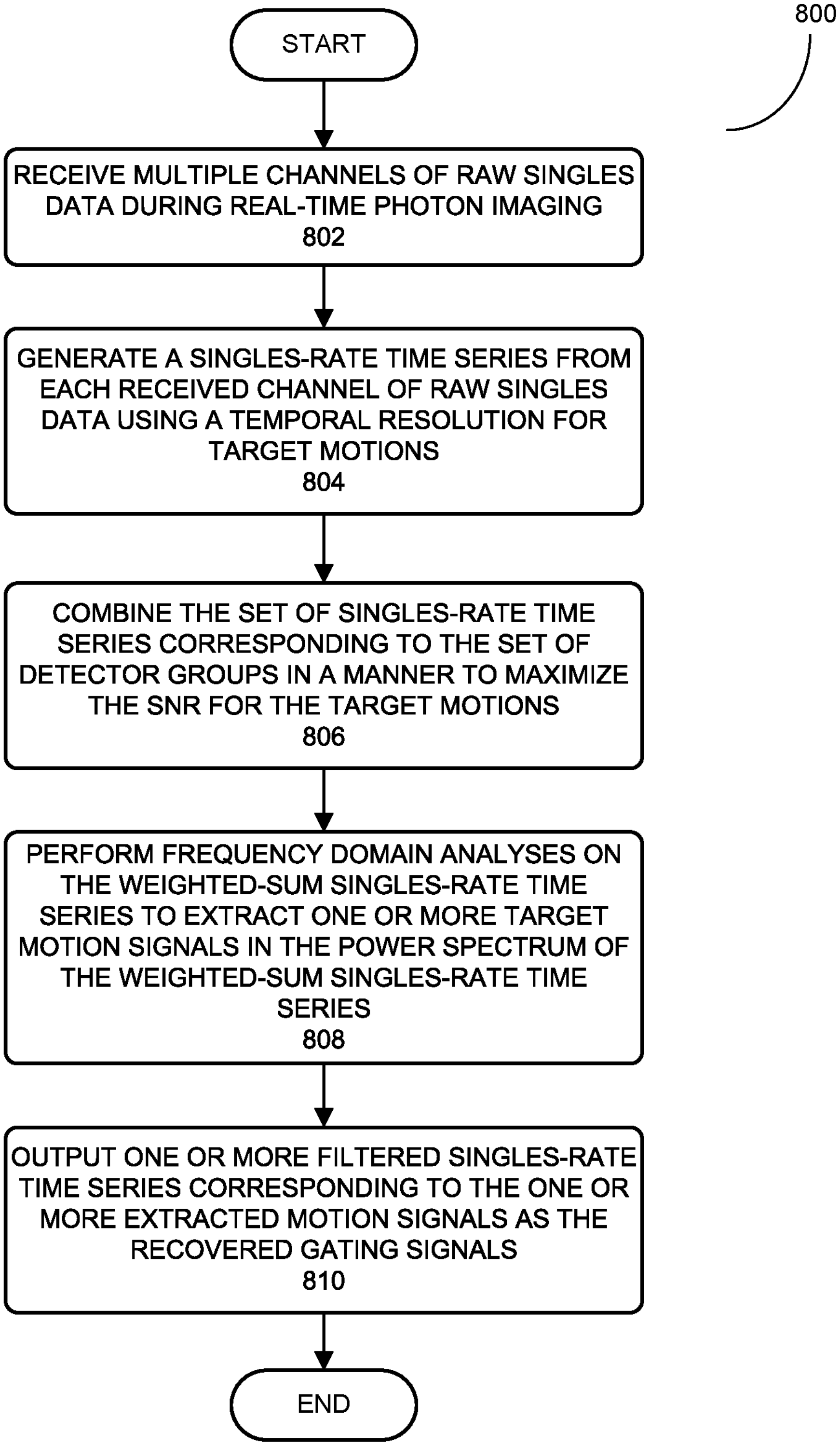
FIG. 8 presents a flowchart illustrating a process of extracting real-time subject-motion signals during photon imaging on a photon scanner, in accordance with the disclosed embodiments.

FIG. 8 presents a flowchart illustrating a process 800 of extracting real-time subject-motion signals during photon imaging on a photon scanner in accordance with the disclosed embodiments. The photon scanner can include any of a PET scanner, a SPECT scanner, a PCCT scanner, an X-ray CT, or a planar/curved gamma camera. The process begins by receiving multiple channels of raw singles data outputted from a set of detector groups of the photon scanner when the photon scanner is performing scans on a live subject (step 802). Note that each channel of raw singles data includes raw time-tagged-count values of the measured singles-events by the array of detectors in the corresponding detector group.

In some embodiments, the multiple channels of raw singles data correspond to a set of axially-arranged detector rings in the photon scanner. However, in the case when the photon scanner contains a single detector ring instead of multiple rings, the blocks of detectors within the single detector module/ring can be first partitioned into a set of groups/sectors of detectors, wherein the partition can be performed along either or both the axial direction and the transaxial direction of the single detector ring. In some embodiments, the partition scheme of the single detector ring along either the axial direction or the transaxial direction can be equal-sized partitions or unequal-sized partitions. For example, when partitioning the single detector ring along the axial direction, smaller partition sizes can be used in the regions of the single detector ring that are closer to the heart and/or the lung region, whereas larger partition sizes can be used in the regions of the single detector ring that are further away from the heart and/or the lung region. Once the single detector ring of the photon scanner is partitioned into a set of detector groups/sectors, each data channel in the received multiple channels of raw singles data then corresponds to a given detector group/sector in the multiple partitioned groups/sectors when the photon scanner is performing scans on the live subject.

Next, process 800 involves generation of a singles-rate time series (i.e., a singles-rate curve) from each received channel of raw singles data using a temporal resolution determined based on the target subject motions (step 804). More specifically, the raw singles data in each data channel, which were recorded at ~1-millisecond resolution, are summed/combined based on the temporal resolution to generate a sequence of singles count values at the temporal resolution. As mentioned above, the temporal resolution may be determined based on the characteristic periods/frequencies of one or more subject motions. For example, a temporal resolution of 0.1 s can be used for tracking both cardiac and respiratory motions.

Next, the singles-rate time series data corresponding to the set of detector groups is combined in a manner to maximize the SNR for the target motions (step 806). In some embodiments, instead of computing a simple sum of the set of singles-rate time series, a weighted sum of the set of singles-rate time series is computed.

Figure 9:
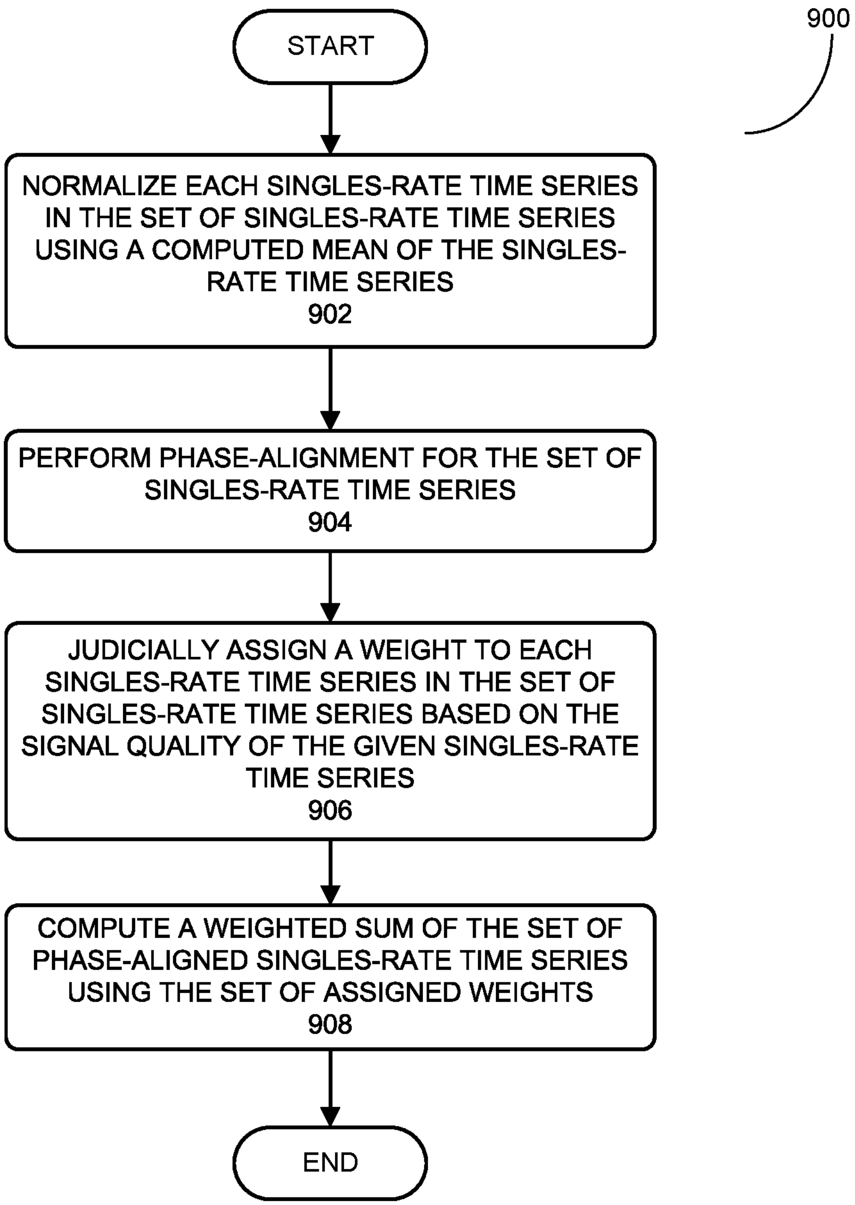
FIG. 9 presents a flowchart illustrating a process of processing the set of singles-rate time series to maximize the SNR, in accordance with the disclosed embodiments.

FIG. 9 presents a flowchart illustrating a process 900 of processing the set of singles-rate time series to maximize the SNR in accordance with the disclosed embodiments. In one or more embodiments, one or more of the steps in FIG. 9 may be omitted, repeated, and/or performed in a different order. Accordingly, the specific arrangement of steps shown in FIG. 9 should not be construed as limiting the scope of the technique.

Process 900 may begin by normalizing each singles-rate time series in the set of singles-rate time series using a computed mean of the singles-rate time series (step 902). Phase-alignment is then performed for the set of singles-rate time series (step 904). Specifically, each and every phase-inverted singles-rate time series in the set of singles-rate time series is first identified. Then, a phase-inversion operation is performed on each identified phase-inverted singles-rate time series. By performing phase-alignment step 902, potential phase cancellation effects when combining the set of singles-rate time series can be eliminated. Next, a weight is judicially assigned to each singles-rate time series in the set of singles-rate time series based on the signal quality of the given singles-rate time series (step 906). In some embodiments, the signal quality is the SNR of the given singles-rate time series. As such, to assign the proper weights, process 900 first computes an SNR of a target motion for each singles-rate time series in the set of singles-rate time series. Process 900 then involves ranking the set of computed SNRs of the set of singles-rate time series in either an ascending order or a descending order. Next, significantly higher weight is assigned to a given ranked time series in the set of singles-rate time series having a higher computed SNR, and a significantly lower weight is assigned to a given ranked time series in the set of singles-rate time series having a lower computed SNR. Next, a weighted sum of the set of phase-aligned singles-rate time series is computed using the set of assigned weights (step 908).

Returning to FIG. 8, after generating a weighted-sum singles-rate time series to significantly improve the SNR, frequency domain analyses on the weighted-sum singles-rate time series are performed to extract one or more target motion signals in the power spectrum of the weighted-sum singles-rate time series (step 808). As mentioned above, one or more band-pass filters can be applied to the power spectrum of the weighted-sum singles-rate time series to filter out one or more portions of the signals-rate signal corresponding to one or more target subject motions. For example, to extract the respiratory motion, a band-pass filter with cut-off frequencies of 0.1-Hz and 0.36-Hz can be applied to the power spectrum of the weighted-sum singles-rate time series. Finally, one or more filtered singles-rate time series corresponding to the one or more extracted motion signals are output as the recovered gating signals (step 810). Note that these filtered output signals can be immediately used as gating signals for reconstructing dynamic photon (e.g., PET or SPECT) scanning images. Also note that by using the real-time process 800, the cardiac motion and respiratory motion signals can be directly extracted in real-time from the raw singles data without the need for any external monitor device (e.g., ECG, EKG, breathing belt, optical markers, etc.).

The disclosed real-time motion-tracking techniques have made possible the performance of high temporal dynamic PET imaging with real-time cardio-respiratory motion gating. Moreover, the disclosed motion-tracking techniques can potentially decouple cardio-respiratory signal from varying activity distributions during the first-pass perfusion (early scan) through the equilibrium state (late scan). The derived motion signals can be useful for characterizing cardiac function, such as mitigating spillover effect between myocardium and blood pool. Using the disclosed techniques, motion-free myocardial extraction fraction can be obtained without motion degradation.

Singles-Based Cardiac Motion Tracking Combined with Deep Learning

We have assumed above that the disclosed singles-based techniques can reliably extract both respiratory motion and cardiac motion signals. However, photon statistics from the heart are generally much smaller than from the large torso region, which means that the direct singles-driven SNR of the heart motion signal is significantly lower than the singles-driven SNR of the respiratory motion signal. More specifically, compared to respiratory motion estimation, there are two challenges for singles-driven cardiac motion tracking: (1) the spatial extent of heart beating is typically much smaller than the respiratory motion affected regions (thoracic and abdominal organs); and (2) the nonspecific cardiac tracers for onco-cardiology may not induce high uptake in heart regions (e.g., for $^{18}$F-FDG). These challenges could result in reduced statistical information and therefore less effectiveness to derive cardiac motion signals from the singles-rate spectrum analysis.

In view of the above challenges to extract the cardiac motion or another weak subject motion embedded in the fluctuation of the singles-rate time series among signals from other organs and various noises, a singles-based deep-learning approach can be used. This deep-learning approach applies a neural network to a time series of two-dimensional (2D) singles-rate maps to extract the cardiac motion or other weaker/smaller subject motions. Note that, different from the above-described one-dimensional (1D) singles-rate time series used for extracting the large organ motions, the inputs to the neural network are a set of raw 2D singles-rate maps outputted from a set of detector groups/modules (e.g., a set of detector rings), wherein each 2D singles-rate map directly corresponds to a 2D detector arrays in the corresponding detector group/module. In other words, the individual singles-rate values from the 2D detector arrays are directly mapped to the individual elements in the 2D singles-rate map, without being combined into a single value like in the above-described 1D singles-rate time series. Consequently, each 2D singles-rate map at a given time step contains positional information pertaining to the scanned subject.

On the other hand, just like in the above-described 1D singles-rate time series, each 2D singles-rate map at a given time step is obtained by summing/combining the recorded raw singles data outputted by individual detectors over a predetermined temporal resolution (e.g., at 0.1 s), thereby forming the time series of the 2D rate maps over time. The underlying features representing the correlation between the time series of 2D singles-rate maps and the periodic organs movement information can then be exploited by learning from existing large datasets. These datasets can include different tracers, diseases, and/or dose levels from which a neural network can be trained to extract cardiac motion signal for any types of photon imaging (e.g., PET) scans.

In some embodiments, a neural network framework for processing the time series of 2D singles-rate maps for cardiac or weak subject motion tracking includes a convolutional neural network (CNN) to extract the most obvious features in a given 2D singles-rate map, which is followed by a recurrent neural network (RNN) or a long short-term memory (LSTM) to forecast temporal features/patterns in the time series of 2D singles-rate maps (e.g., various temporal properties of cardiac cycles). However, in other embodiments of the neural network for processing the time series of 2D singles-rate maps, another neural network framework can be used. For example, an alternative deep neural network for processing the time series of 2D singles-rate maps can include one or more of the following models: a CNN, a RNN, a LSTM, a support vector machine, a decision tree, a Naive Bayes classifier, a Bayesian network, and a k-nearest neighbors (KNN) model.

To implement the proposed deep-learning framework for cardiac motion tracking, the time series of 2D singles-rate maps at a predetermined temporal resolution (e.g., 0.1 s or less) can be acquired and used as an input to the proposed neural network. Meanwhile, a known cardiac phase signal derived from the EKG trace can be acquired and used as ground truth data for training and validating the neural network. Note that the breathing belt can also record a cardiac signal because when the breathing belt is attached to a region between the thorax and abdomen, the breathing belt functions as the stethoscope to record the mechanical waves from the beating heart. As such, a breathing belt may also be used to acquire ground truth data for training and validating the neural network.

Figure 10:
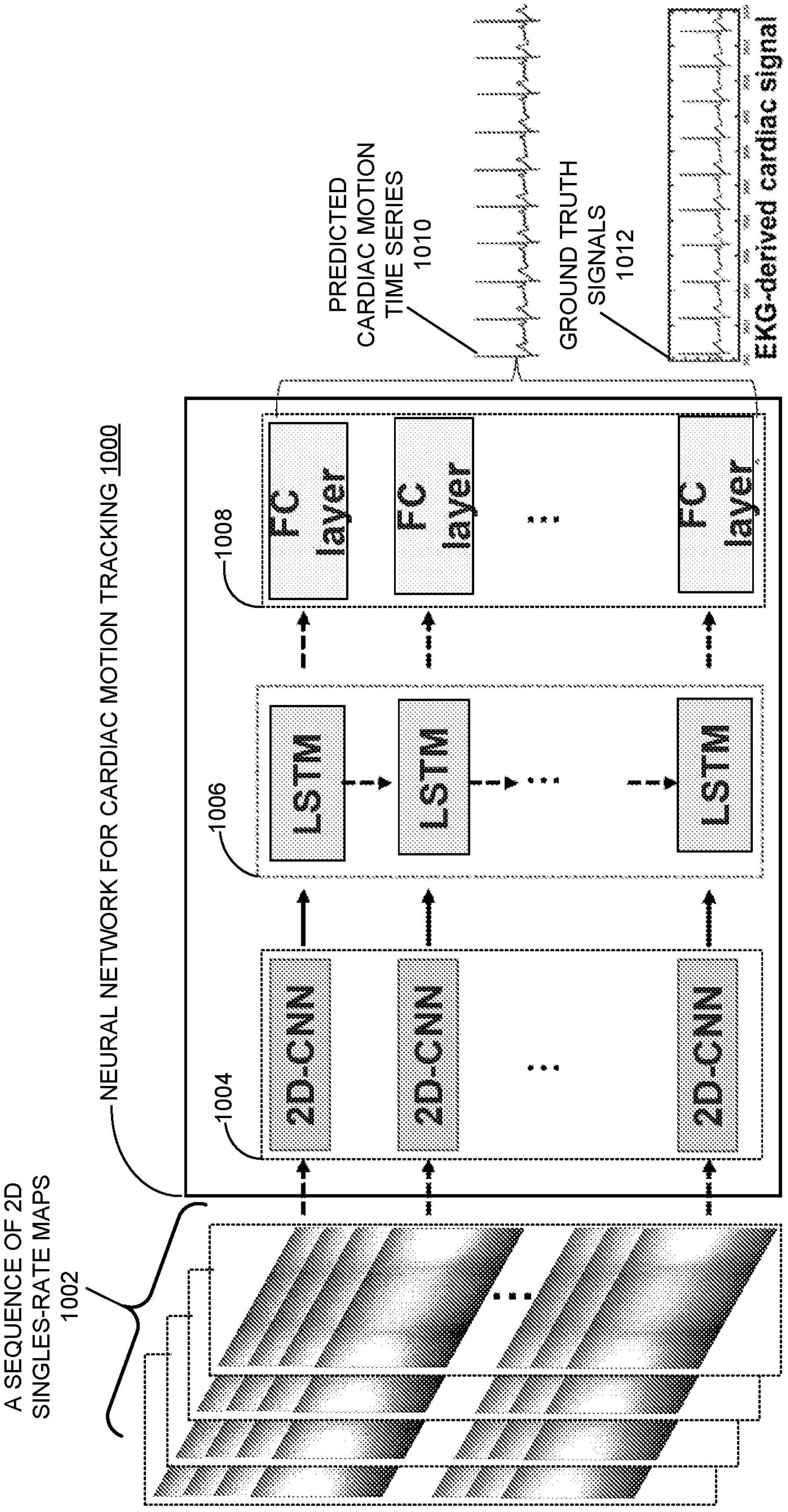
FIG. 10 shows a schematic of the deep-learning neural network for cardiac motion tracking based on input singles-rate maps, in accordance with the disclosed embodiments.

FIG. 10 shows a schematic of deep-learning neural network 1000 for cardiac motion tracking based on a time-series of 2D singles-rate maps 1002, in accordance with the disclosed embodiments. As can be seen in FIG. 10, a sequence of 2D singles-rate maps 1002 at a sequence of time steps is input to the neural network 1000, which will be first processed in parallel by a set of 2D-CNNs 1004 configured with rectified linear activations. Next, the extracted features from the output of 2D-CNN 1004 are fed into a set of LSTM units 1006. The output values of each LSTM unit 1006 can be flattened and fed into a corresponding fully connected (FC) layer 1008 to generate the output values (i.e., the predicted cardiac motion time series 1010). Note that by combining CNNs 1004 and LSTMs 1006 in the proposed deep-learning neural network 1000, the interdependence of data within the input time series data 1002 can be determined. Moreover, automatic denoising for the input 2D singles-rate maps 1002 can be performed to mitigate the challenge of low signal levels. As mentioned above, other neural network frameworks can be used for cardiac motion tracking in place of neural network 1000 shown in FIG. 10. For example, an alternative neural network for processing the input time series of 2D singles-rate maps 1002 can include one or more of a CNN, a RNN, a LSTM, a support vector machine, a decision tree, a Naive Bayes classifier, a Bayesian network, or a k-nearest neighbors (KNN) model.

To prepare and generate the dataset for training neural network 1000, reference signals need to be generated to represent the true cardiac cycles. As mentioned above, ground truth signals 1012 can be derived from measured EKG signals. Note that ground truth signals 1012 can also be obtained from image-driven cardiac motion signals derived from reconstructed sub-second (e.g., 0.1 s) dynamic PET images, which is useful when an EKG signal is not available. To obtain the cardiac motion signal, the time-activity-curves (TAC) of a fixed region of interest (ROI) on myocardium (i.e., heart wall) can be extracted to provide reliable data-driven cardiac phase. In some embodiments, data augmentations such as scaling, flipping, rotation and random brightness can be applied to each training data pair to expand the size of the training dataset.

To validate and quantify the cardiac motion tracking performance of the proposed deep-learning neural network 1000, independent PET scans on multiple human subjects with pronounced myocardium uptakes can be acquired and generated. Next, we can apply deep-learning neural network 1000 containing the hybrid CNN and LSTM to predict the cardiac phases 1010 against the ground truth signals 1012 obtained using EKG or data-driven techniques. Next, we can quantify the error on the end-systolic positions of cardiac phases by tracking the differences between the outputs of neural network 1000 and the ground truth signals.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A computer-implemented method for performing real-time subject-motion tracking during photon imaging on a photon scanner, the method comprising:

receiving multiple channels of raw singles-event data from a set of detector groups of the photon scanner while scanning a live subject;

for each received channel of raw singles-event data, generating a singles-rate time series based on a predetermined temporal resolution of a plurality of predetermined temporal resolutions that are each determined from a characteristic signal frequency associated with one of a plurality of physiological motions of the live subject including at least a cardiac motion of a heart of the live subject and a respiratory motion of a lung of the live subject to generate a set of singles-rate time series associated with each predetermined temporal resolution;

combining the set of singles-rate time series corresponding to the set of detector groups to generate an overall singles-rate time series;

processing the overall singles-rate time series to extract in real-time one or more motion signals corresponding to each of the plurality of physiological motions of the live subject while the live subject is being scanned; and reconstructing a set of real-time dynamic photon scan images corresponding to a set of different phases of the corresponding physiological motion using the one or more extracted motion signals.

2. The computer-implemented method claim 1, wherein the set of detector groups is associated with one or more detector rings arranged along an axial direction of the photon scanner.

3. The computer-implemented method of claim 1, wherein the photon scanner includes a single detector ring formed by a set of detector blocks, and wherein prior to receiving the multiple channels of raw singles-event data, the method further comprising:

partitioning the single detector ring into a set of sectors, wherein each partitioned sector includes a subset of the set of detector blocks; and correlating the set of detector groups to the set of sectors.

4. The computer-implemented method of claim 3, wherein partitioning the single detector ring into a set of sectors further includes using one of the following schemes:

partitioning the single detector ring along an axial direction of the photon scanner;

partitioning the single detector ring along a transaxial direction of the photon scanner; and partitioning the single detector ring along both the axial direction and the transaxial direction of the photon scanner.

5. The computer-implemented method of claim 1, wherein generating the singles-rate time series for a given channel of raw singles-event data based on the predetermined temporal resolution includes:

determining the predetermined temporal resolution based on one or more characteristic signal frequencies or periods associated with the one or more physiological motions; and summing the given channel of raw singles-event data in each predetermined temporal resolution to generate a sequence of singles count values at the predetermined temporal resolution.

6. The computer-implemented method of claim 5, wherein:

the predetermined temporal resolution is significantly smaller than each of the one or more characteristic signal periods; and the predetermined temporal resolution is significantly larger than a singles-event recording resolution used to generate the multiple channels of raw singles-event data.

7. The computer-implemented method of claim 1, wherein combining the set of singles-rate time series to obtain an overall singles-rate time series includes:

normalizing each singles-rate time series in the set of singles-rate time series;

assigning a weight to each singles-rate time series in the set of singles-rate time series based on a signal quality of the given singles-rate time series; and computing a weighted sum of the set of singles-rate time series using the set of assigned weights to obtain the overall singles-rate time series, wherein the overall singles-rate time series has a significantly higher signal to noise ratio (SNR) than a SNR associated with each singles-rate time series in the set of singles-rate time series.

8. The computer-implemented method of claim 7, wherein prior to computing the weighted sum of the set of singles-rate time series, the method further comprises phase-aligning the set of singles-rate time series by:

identifying, in the set of singles-rate time series, each phase-inverted singles-rate time series; and performing a phase-inversion on each identified phase-inverted singles-rate time series.

9. The computer-implemented method of claim 7, wherein assigning the weight to the given singles-rate time series based on the signal quality of the given singles-rate time series includes:

computing an SNR for each singles-rate time series in the set of singles-rate time series;

ranking the set of computed SNRs of the set of singles-rate time series in either an ascending order or a descending order;

assigning a higher weight value to the given singles-rate time series if the given singles-rate time series has a higher computed SNR in the set of computed SNRs; and assigning a lower weight value to the given singles-rate time series if the given singles-rate time series has a lower computed SNR in the set of computed SNRs.

10. The computer-implemented method of claim 1, wherein processing the weighted-sum singles-rate time series to extract in real-time one or more motion signals includes:

identifying a characteristic frequency for each of the one or more physiological motions;

performing a frequency domain analysis on the overall singles-rate time series to obtain a corresponding power spectrum;

filtering the power spectrum around the identified characteristic frequencies to obtain one or more filtered frequency-domain signals corresponding to the one or more physiological motions; and converting the one or more filtered frequency-domain signals into the one or more real-time motion signals in the time domain.

11. The computer-implemented method of claim 1, wherein:

each of the one or more motion signals is a periodic time series; and a given value of the periodic time series at a given time is proportional to the amplitude of the corresponding physiological motion at the given time.

12. The computer-implemented method of claim 1, wherein combining the set of singles-rate time series to generate the overall singles-rate time series includes combining the set of singles-rate time series in a manner to maximize an SNR for the overall singles-rate time series.

13. The computer-implemented method of claim 1, wherein the photon scanner is one of:

a positron emission tomography (PET) scanner;

a single photon emission computed tomography (SPECT) scanner;

a photon-counting computed tomography (PCCT) scanner;

an X-ray CT; and a planar/curved gamma camera.

14. The computer-implemented method of claim 13, wherein the PET scanner includes an extended axial field of view (FOV) to achieve an increased SNR in the generated singles-rate time series.

15. The computer-implemented method of claim 1, wherein the one or more physiological motions of the live subject includes at least one of:

a cardiac motion of a heart of the live subject;

a respiratory motion of a lung of the live subject;

a periodic motion of a non-cardio-respiratory organ of the live subject; and a gross motion of the live subject.

16. The computer-implemented method of claim 1, wherein using the raw singles-event data to perform real-time subject-motion tracking takes place prior to performing coincidence-event sorting.

17. The computer-implemented method of claim 1, wherein the method extracts in real-time the one or more motion signals without using any external monitor device.

18. A photon scanner, comprising:

at least one detector ring;

one or more processors coupled to the at least one detector ring; and a memory coupled to the one or more processors, the memory storing instructions that, when executed by the one or more processors, cause the photon scanner to perform real-time subject-motion tracking during photon imaging on the photon scanner by:

receiving multiple channels of raw singles-event data from a set of detector groups of the at least one detector ring while scanning a live subject;

for each received channel of raw singles-event data, generating a singles-rate time series based on a predetermined temporal resolution of a plurality of predetermined temporal resolutions that are each determined from a characteristic signal frequency associated with one of a plurality of physiological motions of the live subject including at least a cardiac motion of a heart of the live subject and a respiratory motion of a lung of the live subject to generate a set of singles-rate time series associated with each predetermined temporal resolution;

combining the set of singles-rate time series corresponding to the set of detector groups to generate an overall singles-rate time series;

processing the overall singles-rate time series to extract in real-time one or more motion signals corresponding to each of the plurality of physiological motions of the live subject while the live subject is being scanned; and reconstructing a set of real-time dynamic photon scan images corresponding to a set of different phases of the corresponding physiological motion using the one or more extracted motion signals.

19. The photon scanner of claim 18, wherein the at least one detector ring includes a set of detector rings arranged along an axial direction of the photon scanner.

20. The photon scanner of claim 18, wherein the at least one detector ring includes a single detector ring formed by a set of detector blocks, the memory further storing instructions that, when executed by the one or more processors, cause the photon scanner to, prior to receiving the multiple channels of raw singles-event data:

partition the single detector ring into a set of sectors, wherein each partitioned sector includes a subset of the set of detector blocks; and generate the set of detector groups corresponding to the set of sectors.

21. The photon scanner of claim 19, wherein the memory further stores instructions that, when executed by the one or more processors, cause the photon scanner to partition the single detector ring using one of the following schemes:

partitioning the single detector ring along an axial direction of the photon scanner;

partitioning the single detector ring along a transaxial direction of the photon scanner; and partitioning the single detector ring along both the axial direction and the transaxial direction of the photon scanner.

22. The photon scanner of claim 18, wherein the memory further stores instructions that, when executed by the one or more processors, cause the photon scanner to generate the singles-rate time series for a given channel of raw singles-event data by:

determining the predetermined temporal resolution based on one or more characteristic signal frequencies or periods associated with the one or more physiological motions; and summing the given channel of raw singles-event data in each predetermined temporal resolution to generate a sequence of singles count values at the predetermined temporal resolution.

23. The photon scanner of claim 22, wherein:

the predetermined temporal resolution is significantly smaller than each of the one or more characteristic signal periods; and the predetermined temporal resolution is significantly larger than a singles-event recording resolution used to generate the multiple channels of raw singles-event data.

24. The photon scanner of claim 18, wherein the memory further stores instructions that, when executed by the one or more processors, cause the photon scanner to obtain the overall singles-rate time series by:

normalizing each singles-rate time series in the set of singles-rate time series;

assigning a weight to each singles-rate time series in the set of singles-rate time series based on a signal quality of the given singles-rate time series; and computing a weighted sum of the set of singles-rate time series using the set of assigned weights to obtain the overall singles-rate time series, wherein the overall singles-rate time series has a significantly higher signal to noise ratio (SNR) than a SNR associated with each singles-rate time series in the set of singles-rate time series.

25. The photon scanner of claim 24, wherein the memory further stores instructions that, when executed by the one or more processors, cause the photon scanner to phase-align the set of singles-rate time series by, prior to computing the weighted sum of the set of singles-rate time series:

identifying, in the set of singles-rate time series, each phase-inverted singles-rate time series; and performing a phase-inversion on each identified phase-inverted singles-rate time series.

26. The photon scanner of claim 18, wherein the memory further stores instructions that, when executed by the one or more processors, cause the photon scanner to assign the weight to the given singles-rate time series based by:

computing an SNR for each singles-rate time series in the set of singles-rate time series;

ranking the set of computed SNRs of the set of singles-rate time series in either an ascending order or a descending order;

assigning a higher weight value to the given singles-rate time series if the given singles-rate time series has a higher computed SNR in the set of computed SNRs; and assigning a lower weight value to the given singles-rate time series if the given singles-rate time series has a lower computed SNR in the set of computed SNRs.

27. The photon scanner of claim 18, wherein the memory further stores instructions that, when executed by the one or more processors, cause the photon scanner to extract in real-time one or more motion signals by:

identifying a characteristic frequency for each of the one or more physiological motions;

performing a frequency domain analysis on the overall singles-rate time series to obtain a corresponding power spectrum;

filtering the power spectrum around the identified characteristic frequencies to obtain one or more filtered frequency-domain signals corresponding to the one or more physiological motions; and converting the one or more filtered frequency-domain signals into the one or more real-time motion signals in the time domain.

28. The photon scanner of claim 18, wherein:

each of the one or more motion signals is a periodic time series; and a given value of the periodic time series at a given time is proportional to the amplitude of the corresponding physiological motion at the given time.

29. The photon scanner of claim 18, wherein combining the set of singles-rate time series to generate the overall singles-rate time series includes combining the set of singles-rate time series in a manner to maximize the SNR for the overall singles-rate time series.

30. The photon scanner of claim 19, wherein the photon scanner is one of:

a positron emission tomography (PET) scanner;

a single photon emission computed tomography (SPECT) scanner;

a photon-counting computed tomography (PCCT) scanner;

an X-ray CT; and a planar/curved gamma camera.

31. The photon scanner of claim 30, wherein the PET scanner includes an extended FOV to achieve an increased SNR in the generated singles-rate time series.

32. The photon scanner of claim 18, wherein the one or more physiological motions of the live subject includes at least one of:

a cardiac motion of the heart of the live subject;

a respiratory motion of the lung of the live subject;

a periodic motion of a non-cardio-respiratory organ of the live subject; and a gross motion of the live subject.

33. The photon scanner of claim 18, wherein the photon scanner is configured to extract in real-time the one or more motion signals without using any external monitor device.

34. A computer-implemented method for performing motion-free reconstruction of positron emission tomography (PET) images on a PET scanner, the method comprising:

receiving multiple channels of raw singles-event data from a set of detector groups of the PET scanner while scanning a live subject;

for each received channel of raw singles-event data, generating a singles-rate time series based on a predetermined temporal resolution of a plurality of predetermined temporal resolutions that are each determined from a characteristic signal frequency associated with one of a plurality of physiological motions of the live subject including at least a cardiac motion of a heart of the live subject and a respiratory motion of a lung of the live subject to generate a set of singles-rate time series associated with each predetermined temporal resolution;

combining the set of singles-rate time series corresponding to the set of detector groups to generate an overall singles-rate time series;

processing the overall singles-rate time series to extract in real-time a motion signal corresponding to each of the plurality of physiological motions of the live subject while the live subject is being scanned; and reconstruct a set of real-time dynamic PET scan images corresponding to a set of different phases of the corresponding physiological motion using the one or more extracted motion signals.

35. The computer-implemented method of claim 34, wherein:

the real-time motion signal is a periodic time series; and a given value of the periodic time series at a given time is proportional to the amplitude of the corresponding physiological motion at the given time.

36. The computer-implemented method of claim 34, wherein combining the set of singles-rate time series to generate the overall singles-rate time series includes combining the set of singles-rate time series in a manner to maximize an SNR for the overall singles-rate time series.

37. The computer-implemented method of claim 34, wherein the physiological motion of the live subject is one of:

a cardiac motion of the heart of the live subject;

a respiratory motion of the lung of the live subject;

a periodic motion of a non-cardio-respiratory organ of the live subject; and a gross motion of the live subject.

38. The computer-implemented method of claim 34, wherein processing the overall singles-rate time series to extract the motion signal includes using a deep neural network when the corresponding physiological motion is the cardiac motion or another physiological motion of a small organ.

* * * * *